（12）United States Patent
Lewis et al.

(10) Patent No.: US 12,186,393 B2
(45) Date of Patent: *Jan. 7, 2025

(54) METHOD OF TREATING TRANSITIONAL CELL CARCINOMA IN A CANINE BY ADMINISTERING LAPATINIB, WHEREIN THE CARCINOMA HARBORS A BRAF MUTATION

(71) Applicant: ONEHEALTHCOMPANY, INC., Palo Alto, CA (US)

(72) Inventors: Benjamin Lewis, Palo Alto, CA (US); Christina Kelly Lopes, Palo Alto, CA (US); Lindsay Lambert, Palo Alto, CA (US); Garrett Harvey, Palo Alto, CA (US); Thaddeus A. Allen, Palo Alto, CA (US); Aubrey Miller, Palo Alto, CA (US); Lucas Rodrigues, Palo Alto, CA (US); Madison Luker, Palo Alto, CA (US); Gerald Post, Palo Alto, CA (US)

(73) Assignee: ONEHEALTHCOMPANY, INC., Palo Alto, CA (US)

( * ) Notice: Subject to any disclaimer, the term of this patent is extended or adjusted under 35 U.S.C. 154(b) by 298 days.

This patent is subject to a terminal disclaimer.

(21) Appl. No.: 17/632,327

(22) PCT Filed: Aug. 2, 2020

(86) PCT No.: PCT/US2020/044689
§ 371 (c)(1),
(2) Date: Feb. 2, 2022

(87) PCT Pub. No.: WO2021/026046
PCT Pub. Date: Feb. 11, 2021

(65) Prior Publication Data
US 2022/0354951 A1 Nov. 10, 2022

Related U.S. Application Data

(60) Provisional application No. 62/909,098, filed on Oct. 1, 2019, provisional application No. 62/906,924, filed on Sep. 27, 2019, provisional application No. 62/904,987, filed on Sep. 24, 2019, provisional application No. 62/902,889, filed on Sep. 19, 2019, provisional application No. 62/901,185, filed on Sep. 16, 2019, provisional application No. 62/899,932, filed on Sep. 13, 2019, provisional application No. 62/898,888, filed on Sep. 11, 2019, provisional application No. 62/897,872, filed on Sep. 9, 2019, provisional application No. 62/882,401, filed on Aug. 2, 2019.

(51) Int. Cl.
*A61K 41/00* (2020.01)
*A61K 31/519* (2006.01)
*A61P 35/00* (2006.01)
*A61P 35/02* (2006.01)
*A61K 31/517* (2006.01)
*A61K 39/00* (2006.01)

(52) U.S. Cl.
CPC .......... *A61K 41/00* (2013.01); *A61K 31/519* (2013.01); *A61P 35/02* (2018.01); *A61K 31/517* (2013.01); *A61K 2039/505* (2013.01); *A61P 35/00* (2018.01)

(58) Field of Classification Search
CPC .............. A61K 41/00; A61K 2039/505; A61P 35/00; A61P 35/02
See application file for complete search history.

(56) References Cited

U.S. PATENT DOCUMENTS

| 6,596,746 | B1 | 7/2003 | Das et al. |
| 6,894,051 | B1 | 5/2005 | Zimmermann et al. |
| 6,958,335 | B2 | 10/2005 | Buchdunger et al. |
| 7,125,875 | B2 | 10/2006 | Das et al. |
| 7,153,856 | B2 | 12/2006 | Barrish et al. |
| 7,235,576 | B1 | 6/2007 | Riedl et al. |
| 7,351,834 | B1 | 4/2008 | Riedl et al. |
| 7,378,423 | B2 | 5/2008 | Kawasaki et al. |
| 7,399,787 | B2 | 7/2008 | Chiao et al. |

(Continued)

FOREIGN PATENT DOCUMENTS

| WO | 2018/229132 A1 | 12/2018 |
| WO | 2021/026046 A1 | 2/2021 |

OTHER PUBLICATIONS

Sakai K, et al. (Dec. 2018) Vet Comp Oncol. 6(4):642-649 (doi: 10.1111/vco.12434. Epub Sep. 23, 2018).*
Baskar R, et al. (2012) Int J Med Sci. 9(3):193-199. (Published online Feb. 27, 2012. doi: 10.7150/ijms.3635).*
Mochizuki H, et al. (2015) PLoS One. 10(6): e0129534. (Published online Jun. 8, 2015. doi: 10.1371/journal.pone.0129534).*
Laboklin actuell (Oct. 2019) BRAF mutation in canine transitional cell and prostate carcinoma. 3 pages.*
Burris, III Ha, et al. (Nov. 1, 2009) Clin Cancer Res. 15(21):6702-6708. (Published online Oct. 13, 2009. doi: 10.1158/1078-0432. CCR-09-0369).*
Findlay et al., "On the Chemistry and High Field Nuclear Magnetic Resonance Spectroscopy of Rapamycin," Can. J. Chem. 58, pp. 579-590, 1980.

(Continued)

*Primary Examiner* — Robert S Landsman
(74) *Attorney, Agent, or Firm* — Goodwin Procter LLP

(57) ABSTRACT

Described herein are methods useful for the treatment of cancers in a canine subject with a pharmaceutical compositions comprising HD AC inhibitors, Rapamycin, Dasatinib, Lapatinib, Trametinib, Vorinostat, Imatinib, Crizotinib, Sorafenib, and combinations thereof. Also described herein are methods for identification of subjects with cancers that will benefit from administration of the pharmaceutical compositions comprising HD AC inhibitors, Rapamycin, Dasatinib, Lapatinib, Trametinib, Vorinostat, Imatinib, Crizotinib, Sorafenib, and combinations thereof. In certain aspects, the methods described herein further comprise administering a therapeutically effective amount of at least one additional anti-cancer agent.

20 Claims, 12 Drawing Sheets

(56) References Cited

U.S. PATENT DOCUMENTS

| | | | |
|---|---|---|---|
| 7,456,219 | B2 | 11/2008 | Miller et al. |
| 7,491,725 | B2 | 2/2009 | Lajeunesse et al. |
| 7,652,069 | B2 | 1/2010 | Miller et al. |
| 7,732,490 | B2 | 6/2010 | Richon et al. |
| 7,825,137 | B2 | 11/2010 | Christensen et al. |
| 7,851,509 | B2 | 12/2010 | Miller et al. |
| 7,858,643 | B2 | 12/2010 | Cui et al. |
| 7,897,623 | B2 | 3/2011 | Riedl et al. |
| 8,067,472 | B2 | 11/2011 | Richon et al. |
| 8,093,295 | B2 | 1/2012 | Wong et al. |
| 8,101,663 | B2 | 1/2012 | Miller et al. |
| 8,124,630 | B2 | 2/2012 | Riedl et al. |
| 8,217,057 | B2 | 7/2012 | Cui et al. |
| 8,450,372 | B2 | 5/2013 | Wong et al. |
| 8,580,304 | B2 | 11/2013 | DeMarini et al. |
| 8,618,141 | B2 | 12/2013 | Dumas et al. |
| 8,680,103 | B2 | 3/2014 | Lajeunesse et al. |
| 8,703,781 | B2 | 4/2014 | Dumble et al. |
| 8,785,632 | B2 | 7/2014 | Cui et al. |
| 8,835,443 | B2 | 9/2014 | Kawasaki et al. |
| 8,841,330 | B2 | 9/2014 | Riedl et al. |
| 8,877,933 | B2 | 11/2014 | Grunenberg et al. |
| 8,952,018 | B2 | 2/2015 | Dumble et al. |
| 9,155,706 | B2 | 10/2015 | DeMarini et al. |
| 9,271,941 | B2 | 3/2016 | DeMarini et al. |
| 9,737,488 | B2 | 8/2017 | Schuckler et al. |
| 12,036,281 | B2 | 7/2024 | Lewis et al. |
| 2006/0100286 | A1 | 5/2006 | Cohen et al. |
| 2016/0143946 | A1 | 5/2016 | Chin |
| 2017/0209467 | A1 | 7/2017 | Vancurova et al. |

OTHER PUBLICATIONS

Notification of Transmittal of the International Search Report and the Written Opinion of the International Searching Authority, or the Declaration, Int'l Application No. PCT/US2020/44689, mailed Dec. 22, 2020, 31 pages.

Thurn et al., Histone Deacetylase Regulation of ATM-Mediated DNA Damage Signaling,: Mol Cancer Ther. Oct. 2013, vol. 12, No. 10, pp. 2078-2087.

Amanda Foskett, Christina Manley, Rebecca Naramore, Ira K Gordon, Bridget M Stewart & Chand Khanna (2017) Tolerability of oral sorafenib in pet dogs with a diagnosis of cancer, Veterinary Medicine: Research and Reports, 8:, 97-102, DOI: 10.2147/VMRR. S149678.

Henry, Carolyn J. et al, "Clinical Evaluation of Mitoxantrone and Piroxicam in a Canine Model of Human Invasive Urinary Bladder Carcinoma", Clinical Cancer Research, vol. 9, Feb. 2003, p. 906-911.

Extended European Search Report issued Oct. 10, 2023 in European Application No. 20850752.5.

Elbadawy, Mohamed et al, "Anti-tumor effect of trametinib in bladder cancer organoid and the underlying mechanism," Oct. 20, 2020.

De Vos J, Ramos Vega S, Noorman E, De Vos P. Primary frontal sinus squamous cell carcinoma in three dogs treated with piroxicam combined with carboplatin or toceranib. Veterinary and comparative oncology. Sep. 2012;10(3):206-13.—piroxicam-toceranib for SCC. Communication pursuant to rules 70(2) and 70a(2) issued Oct. 27, 2023 in European Application No. 20850752.5.

Chun, Ruthanne et al, "Phase II Clinical Trial of Carboplatin in Canine Transitional Cell Carcinoma of the Urinary Bladder", Journal of Veterinary Internal Medicine, vol. 11, No. 5, Sep.-Oct. 1997, p. 279-283.

Cawley, Jacob R. et al, "Pharmacokinetic Exposures Associated With Oral Administration of Sorafenib in Dogs With Spontaneous Tumors," Front. Vet. Sci., vol. 9, May 19, 2022.

Bongiovanni L, Andriessen A, Silvestri S, Porcellato I, Brachelente C, de Bruin A. H2AFZ: A Novel Prognostic Marker in Canine Melanoma and a Predictive Marker for Resistance to CDK4/6 Inhibitor Treatment. Front Vet Sci. Aug. 16, 2021;8:705359. doi: 10.3389/fvets.2021.705359. PMID: 34485433; PMCID: PMC8415453.

Arnold, E.J. et al, "Clinical Trial of Vinblastine in Dogs with Transitional Cell Carcinoma of the Urinary Bladder", J Vet Intern Med, 2011, 25, p. 1385-1390.

Anonymous, "SAHA (Vorinostat)", Jul. 26, 2017, pp. 1-1, XP093058993.

Andersen, Nicholas J. et al, "Pharmacologic Inhibition of MEK Signaling Prevents Growth of Canine Hemangiosarcoma," Molecular Cancer Therapeutics, vol. 12, Issue 9, 1701-1714, Sep. 1, 2013.

London et al., "Tyrosine Kinase Inhibitors in Veterinary Medicine," Topics in Companion Animal Medicine, Elsevier, Amsterdam, NL, vol. 24, No. 3, Aug. 1, 2009, pp. 106-112, XP026562343.

Maeda, Shingo et al, "Lapatinib as first-line treatment for muscle-invasive urothelial carcinoma in dogs", Scientific Reports, 2022 (12:4) <https://doi.org/10.1038/s41598-021-04229-0>.

Marconato, Laura et al, "Sorafenib for the Treatment of Unresectable Hepatocellular Carcinoma: Preliminary Toxicity and Activity Data in Dogs," Cancers (Basel), May 2020, 12(5): 1272.

Mohammed, Sulma I. et al, "Effects of the Cyclooxygenase Inhibitor, Piroxicam, on Tumor Response, Apoptosis, and Angiogenesis in a Canine Model of Human Invasive Urinary Bladder Cancer", Cancer Research 62, Jan. 15, 2002, p. 356-358.

Nieset, J.R., Harmon, J.F., Johnson, T.E. and Larue, S.M. (2014), Comparison of adaptive Radiotherapy Techniques for external radiation therapy of canine bladder cancer. Vet Radiol Ultrasound, 55: 644-650. https://doi.org/10.1111/vru.12163.

Owner Handout: Palladia, The Ohio State University Veterinary Medical Center Oncology Service, Hospital for Companion Animals, <https://vet.osu.edu/vmc/sites/default/files/images/Palladia%20Ohio%20State%20VMC%20print.pdf>, Accessed: Nov. 13, 2023.

Partial supplementary European Search Report dated Jul. 7, 2023 issued in European Application No. 20850752.5.

Wei BR, Peer CJ, Richardson WJ, Hewitt SM, Figg WD, Simpson RM. Pharmacokinetics and tolerability of the dual TORC1/2 inhibitor sapanisertib in combination with the MEK inhibitor trametinib in dogs. Front Vet Sci. Dec. 14, 2022;9:1056408. doi: 10.3389/fvets.2022.1056408. PMID: 36590793; PMCID: PMC9794608.

El Karak et al., "Gemcitabine in bladder Cancer," Expert Opin. Pharmacother. (2007) 8(18):3251-3256.

K. Sakai et al. Anti-tumour effect of lapatinib in canine transitional cell carcinoma cell lines. Vet Comp Oneal. 2018;16:642-649.

G.V. Long et al., "Adjuvant Dabrafenib plus Tramentinib in Stage III BRAF-Mutated Melanoma," N Engl J Med. vol. 377;19. pp. 1813-1823, Nov. 9, 2017.

Weisse, Chick et al, "Evaluation of palliative stenting for management of malignant urethral obstructions in dogs", J Am Vet Med Assoc, vol. 229, No. 2, Jul. 15, 2006.

Thumser-Henner, Pauline et al, "Mutations of BRCA2 in canine mammary tumors and their targeting potential in clinical therapy," BMC Veterinary Research, 16:30, Jan. 31, 2020.

Zompoulidou, Georgia et al, "Therapeutic vulnerability to PARP1,2 inhibition in RB1-mutant osteosarcoma," Nature Communications, 12, Article No. 7064 (2021).

T. Powles et al., "Phase III, Double-Blind, Randomized Trial That Compared Maintenance Lapatinib Versus Placebo After First-Line Chemotherapy in Patients With Human Epidermal Growth Factor Receptor 1/2-Positive Metastatic Bladder Cancer" J Clin Oncology, vol. 35, 1, pp. 1-11, 2016.

U.S. Appl. No. 18/304,883, filed Apr. 21, 2023, Pending.

\* cited by examiner

METHOD OF TREATING TRANSITIONAL CELL CARCINOMA IN A CANINE BY ADMINISTERING LAPATINIB, WHEREIN THE CARCINOMA HARBORS A BRAF MUTATION

CROSS REFERENCE TO RELATED APPLICATIONS

This application is a U.S. National Phase Application of International Application No. PCT/US2020/044689 filed Aug. 2, 2020, which claims priority under 35 U.S.C. § 119(e) to U.S. Provisional Application Nos. 62/882,401 filed Aug. 2, 2019; 62/897,872 filed Sep. 9, 2019; 62/898,888 filed Sep. 11, 2019; 62/899,932 filed Sep. 13, 2019; 62/901,185 filed Sep. 16, 2019; 62/902,889 filed Sep. 19, 2019; 62/904,987 filed Sep. 24, 2019; 62/906,924 filed Sep. 27, 2019 and 62/909,098 filed Oct. 1, 2019; which are hereby incorporated by reference in their entirety.

REFERENCE TO A SEQUENCE LISTING XML

This application contains a Sequence Listing which has been submitted electronically in XML format. The Sequence Listing XML is incorporated herein by reference. Said XML file, created on Jun. 27, 2023, is named OHC-001USC1_SL.xml and is 3,128 bytes in size.

BACKGROUND

Disclosed herein are methods and compositions useful for the treatment of cancers in a canine subject with various compositions comprising targeted anti-cancer agents, including HDAC inhibitors, Rapamycin, Dasatinib, Lapatinib, Trametinib, Vorinostat, Imatinib, Crizotinib, Sorafenib, and combinations thereof.

Rapamycin is an inhibitor of mTOR (mammalian target of Rapamycin), a key protein in the PI3K/Akt pathway that has two different multiprotein complexes: mTORC1 and mTORC2 (FIG. 4). Increased activation of mTORC1 is observed in numerous cancers due to gain-of-function mutations in oncogenes (e.g., PI3K, AKT, or Ras). mTORC1 serves as a central regulator of cell metabolism, growth, proliferation and survival. Rapamycin has a more complex effect on mTORC2, inhibiting it only in certain cell types under prolonged exposure. Increased activity of PI3K/Akt pathway is often associated with tumor progression and resistance to cancer therapies. Rapamycin binds simultaneously to the FKBP and FRB domains of mTORC1 and acts both upstream and downstream of AKT. S6K1 and 4E-BP1 are two well characterized substrates phosphorylated by mTORC1 implicated in transcription, translation, impacting protein and lipid synthesis and are critical for cell growth and metabolism.

Dasatinib is an oral synthetic small molecule-inhibitor of SRC-family protein-tyrosine kinases ("SRC family kinases") (FIG. 5), as well as other tyrosine kinases, including, ABL, BCR-ABL, c-KIT, EPHA2 and PDGFR. Dasatinib has binding activity to a highly conserved ATP binding site occupancy of which by the drug locks these tyrosine kinases into an inactive state. SRC-family protein-tyrosine kinases and BCR-ABL are non-receptor tyrosine kinases that play important roles in angiogenesis and cellular proliferation of solid and hematological malignancies. SRC family kinases, BCR-ABL and PDGFR play important roles in regulating mitotic events and activating JAK-STAT, PI3K/AKT and MAPK/ERK signaling pathways that are critical to tumor cells' proliferation and survival. SRC is overexpressed in a variety of solid tumors, while BCR-ABL is the causative agent of canine and human chronic myeloid leukemia (CML).

Lapatinib is a tyrosine kinase inhibitor that has efficacy in animal models and human clinical trials of cancer where the growth factor receptors ERBB1 (epidermal growth factor receptor, EGFR) and ERBB2 (HER2) contribute to carcinogenesis. The anti-tumor effect of lapatinib is mediated by selective binding to the adenosine triphosphate (ATP) binding pocket of its target receptor tyrosine kinases. This prevents receptor activation through autophosphorylation and prevents further downstream signaling resulting in inhibition of tumor cell proliferation and survival. Lapatinib works high in the EGFR signaling cascade by targeting both the ERBB1 and ERBB2 proteins (FIG. 6). Lapatinib is able to prevent auto-phosphorylation of these receptor tyrosine kinases, thereby negating downstream signaling cascades. Of particular importance, are the MEK/ERK and PI3K/AKT pathways that enhance the proliferation and survival of cancer cells.

Trametinib is a small molecule, non-receptor tyrosine kinase inhibitor. Trametinib is a reversible, selective, allosteric inhibitor of MEK1/MEK2 activation and kinase activity. In vitro studies have demonstrated that trametinib decreases cell proliferation, causes G1 cell cycle arrest, and induces apoptosis. Trametinib inhibits components of one of the MAP kinase cascades that emanate from upstream receptor tyrosine kinases (FIG. 7). Depicted here is the epidermal growth factor receptor, but multiple upstream regulators can activate MEK signaling in the same cell. RAS and RAF proto-oncogenes lie proximally in the cascade but even cancers without activated forms of these oncogenes can have constitutive MEK activation.

Vorinostat is a small molecule, tyrosine kinase inhibitor. Vorinostat is a synthetic hydroxamic acid used orally as a histone deacetylase (HDACs) inhibitor and antineoplasic agent. Vorinostat promotes cell-cycle arrest and apoptosis of cancer cells through regulation of gene expression. Numerous HDACs defects leading to reduced or abnormal acetylation have been identified in leukemia, lymphoma and solid tumor cell lines. These defects include mutation, translocation and overexpression of p300, CBP, TIF-2, RAR, BCL-6, AML1, STAT5 and HDAC1. Vorinostat crosses the blood-brain barrier. Vorinostat inhibits hyperacetylation of histone proteins leading to upregulation of p21 followed by G1 arrest. Hyperacetylation of p53 produces additional anti-proliferative effects. Vorinostat is recommended in tumors with MYC overexpression due to the regulatory effects on HDACs (FIG. 8).

Imatinib is a tyrosine kinase inhibitor used to treat human and animals with cancer. This small molecule works at the ATP binding site of ABL, BCR-ABL, PDGFR, and C-KIT, thereby inhibiting the kinase activity of these proteins. This binding activity blocks downstream signaling that can be important in the maintenance of cell proliferation and survival. Imatinib binds to BCR-ABL, PDGFR and C-KIT, among other targets (FIG. 9). This can abrogate the ability of these kinases to stimulate mitogen-activated kinases (RAF, MEK and MAPK) and the JAK-STAT and PI3K/AKT pathways. These pathways can be essential in maintaining cell proliferation and survival. Accordingly, this drug can potentially decrease cell proliferation, migration and angiogenesis and enhance apoptosis.

Crizotinib is a tyrosine kinase inhibitor of ALK, c-MET and ROS1. The formation of ALK-EML4 fusion protein results in the activation of RAS/MAPK, PI3K/AKT, JAK and STAT pathways that play significant roles in cancer development. Crizotinib is able to bind to ALK protein preventing the activation of these downstream pathways. c-MET is a transmembrane tyrosine kinase receptor activated by hepatocyte growth factor (HGF) ligand implicated in the progression of several cancers. The inhibitory effect of crizotinib on c-MET has been shown to inhibit AKT and ERK signaling leading tumor cell to apoptosis. Crizotinib acts on ATP-binding site of ALK-EML4 fusion protein and ROS1. Pathways downstream ALK and ROS1 are PI3K/AKT/mTOR, JAK/STAT and MAPK/ERK that promote proliferation and cell survival. Crizotinib inhibits c-MET activation avoiding the phosphorylation of adaptor proteins such as GRB2, GAB1, SRC, ShC and c-CBL and subsequente PI3K, AKT, STAT and ERK (FIG. 10).

Sorafenib is an oral multikinase inhibitor that targets the 3 RAF serine/threonine kinase isoforms (ARAF, BRAF and CRAF), collectively shown as "Raf" in FIG. 11, that regulates fundamental cellular processes including growth, differentiation and survival. All RAF proteins are activated by RAS and subsequently activate MEK, initiating the signal transduction cascade of the MAPK pathway. Sorafenib also inhibits the oncogenic BRAF V600E, responsible for abnormal proliferation and differentiation, and tyrosine kinase receptors such as VEGFRs (VEGFR-1, VEGFR-2, VEGFR-3) PDGFR-β, RET and c-KIT (as well as Flt-3, not shown in FIG. 11), implicated in tumorigenesis and tumor progression The multisite activity of this small molecule explains its broad preclinical activity across tumor types. Sorafenib blocks receptor tyrosine kinase signaling (VEGFR, PDGFR-β c-KIT and RET) and inhibits downstream Raf serine/theorine kinase (ARAF, BRAF, mutant BRAF V600E and CRAF) activity to prevent tumor growth by antiangiogenic, antiproliferative and pro-apoptotic effects. (FIG. 11).

Although targeted anti-cancer agents have been effective in the treatment of some human cancers, these agents are generally exhibit unpredictable efficacy, especially. in canines. Therefore, there is a need for improved methods and compositions for predicting efficacy and treating cancers in canine subjects with targeted anti-cancer agents.

SUMMARY

In certain aspects, described herein is a method of treating a subject with cancer comprising the step of administering a therapeutically effective amount of a histone deacetylase complex (HDAC) inhibitor to a subject having a cancer harboring at least one mutation in ataxia-telangiectasia mutated (ATM) kinase. In certain embodiments, the method includes the step of identifying the mutation in a sample derived from the subject. In certain embodiments, the HDAC inhibitor is selected from the group consisting of: romidepsin, belinostat, panobinostat, vorinostat, givinostat, entinostat, tacedinaline, and mocetinostat. In certain embodiments, the HDAC inhibitor is vorinostat. In certain embodiments, the method, further comprises administering an effective amount of a DNA damaging chemotherapeutic agent. In certain embodiments, the DNA damaging chemotherapeutic agent is selected from the group consisting of a DNA-alkylating agent, DNA crosslinking agent, antimetabolite, topoisomerase inhibitor and a DNA intercalating agent. In certain embodiments, the DNA-alkylating agent is selected from the group consisting of a nitrosourea, a triazene and a platinum agent. In certain embodiments, the DNA-alkylating agent is a nitrosourea. In certain embodiments, the nitrosourea is lomustine. In certain embodiments, the method, further comprises performing surgery on the subject. In certain embodiments, the method further comprises administering an effective amount of at least one additional anti-cancer therapeutic agent. In certain embodiments, the method further comprises administering to the subject ionizing radiation. In certain embodiments, the cancer harbors more than one mutant allele of ATM kinase. In certain embodiments, the biological sample is a nucleic acid sample. In certain embodiments, the biological sample is a purified nucleic acid sample. In certain embodiments, the sample is DNA. In certain embodiments, the sample is RNA. In certain embodiments, the identifying is performed by sequencing a nucleic acid sample. In certain embodiments, the cancer is cancer in a canine subject. In certain embodiments, the cancer is selected from the group consisting of solid tumor, lymphoma, cutaneous T-cell lymphoma, peripheral T-cell lymphoma, sarcoma, histiocytic sarcoma, multiple myeloma, hemangiosarcoma, lymphosarcoma, osteosarcoma, mammary carcinoma, melanoma, mast cell tumors, lipoma, anal gland adenocarcinoma, lung cancer and thyroid cancer. In certain embodiments, the cancer is histiocytic sarcoma.

In certain aspects, described herein is a method of treating a subject with a cancer harboring at least one mutation in ATM kinase. In certain embodiments, the method further comprises determining or having determined at least one mutation in ATM kinase in a in a sample derived from the cancer. In certain embodiments, the method comprises administering to the subject a therapeutically effective amount of a histone deacetylase complex (HDAC) inhibitor. In certain embodiments, the HDAC inhibitor is vorinostat. In certain embodiments, the methods further comprise administering a DNA damaging chemotherapeutic agent. In certain embodiments, the DNA damaging chemotherapeutic agent is lomustine. In certain embodiments, at least one mutation in ATM kinase is selected from: a missense mutation, a splice site mutation and a frameshift variant. In certain embodiments, at least one mutation in ATM kinase inhibits ATM kinase activity.

In certain embodiments, described herein are methods of treating cancer in a canine subject comprising, administering to a subject in need thereof a therapeutically effective amount of a pharmaceutical composition comprising Rapamycin. In certain aspects, the Rapamycin is administered at a dose equal to or less than 1 mg/kg. In certain aspects, the Rapamycin is administered at a dose of 0.05-0.1 mg/kg. In certain aspects, the pharmaceutical composition is administered at a frequency selected from the group consisting of twice daily, once daily, once every other day, once every third day, once every fourth day, once every $5^{th}$ day, or weekly. In certain aspects, the Rapamycin is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetabolite, topoisomerase inhibitor and a DNA intercalating agent. In certain aspects, at least one additional anti-cancer agent is a targeted anti-cancer agent. In certain aspects, the targeted anti-cancer agent is selected from the group consisting of Crizotinib, Dasatinib Erlotinib, Gefinitib, Imatinib, Lapatinib, Sorafenib, Trametinib, and Vorinostat. In certain aspects, the targeted anti-cancer agent is Dasatinib. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of mTOR, PI3K, AKT and Ras. In certain aspects, the methods described herein further comprise having determined from a biological sample derived from the cancer, that the cancer harbors a mutation in at least one gene selected from the group consisting of mTOR, PI3K, AKT and Ras. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in at least one gene is performed by sequencing the nucleic acid sample. In certain aspects, the cancer in the canine subject is selected from the group consisting of: solid tumor, leukemia, lymphocytic leukemia, lymphoma, sarcoma, multiple myeloma, hemangiosarcoma, histiocytic sarcoma, lymphosarcoma, osteosarcoma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer and thyroid cancer. In certain aspects, the cancer is hemangiosarcoma. In certain embodiments, described herein are pharmaceutical compositions formulated for oral administration, comprising Rapamycin, wherein the Rapamycin is present at a concentration of 0.001 mg/mL-10.0 mg/mL.

In certain embodiments, described herein are methods of treating cancer in a canine subject comprising, administering to a subject in need thereof a therapeutically effective amount of a pharmaceutical composition comprising Dasatinib. In certain aspects, the Dasatinib is administered at a dose equal to or less than 2 mg/kg. In certain aspects, the Dasatinib is administered at a dose of 0.5-0.7 mg/kg. In certain aspects, the pharmaceutical composition is administered at a frequency selected from the group consisting of twice daily, once daily, once every other day, once every third day, once every fourth day, once every $5^{th}$ day, or weekly. In certain aspects, the Dasatinib is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetabolite, topoisomerase inhibitor and a DNA intercalating agent. In certain aspects, at least one additional anti-cancer agent is a targeted anti-cancer agent. In certain aspects, the targeted anti-cancer agent is selected from the group consisting of: Crizotinib, Rapamycin, Erlotinib, Gefinitib, Imatinib, Lapatinib, Sorafenib, Trametinib, and Vorinostat. In certain aspects, the targeted anti-cancer agent is Rapamycin. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of ABL, BCR-ABL, c-KIT, EPHA2, PDGFR and a Src Family Kinase. In certain aspects, the methods described herein further comprise having determined from a biological sample derived from the cancer, that the cancer harbors a mutation in at least one gene selected from the group consisting of ABL, BCR-ABL, c-KIT, EPHA2, PDGFR and a Src Family Kinase. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in at least one gene is performed by sequencing the nucleic acid sample. In certain aspects, the cancer in the canine subject is selected from the group consisting of solid tumor, leukemia, lymphocytic leukemia, lymphoma, sarcoma, multiple myeloma, hemangiosarcoma, histiocytic sarcoma, lymphosarcoma, osteosarcoma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer and thyroid cancer. In certain aspects, the cancer is osteosarcoma. In certain embodiments, described herein are pharmaceutical compositions formulated for oral administration, comprising Dasatinib, wherein the Dasatinib is present at a concentration of 0.001 mg/mL-10.0 mg/mL.

In certain embodiments, described herein are methods of treating cancer in a canine subject comprising, administering to a subject in need thereof a therapeutically effective amount of a pharmaceutical composition comprising Lapatinib. In certain aspects, the Lapatinib is administered at a dose equal to or less than 50 mg/kg. In certain aspects, the Lapatinib is administered at a dose of 5 mg/kg-10 mg/kg. In certain aspects, the pharmaceutical composition is administered at a frequency selected from the group consisting of twice daily, once daily, once every other day, once every third day, once every fourth day, once every $5^{th}$ day, or weekly. In certain aspects, the Lapatinib is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetabolite, topoisomerase inhibitor and a DNA intercalating agent. In certain aspects, at least one additional anti-cancer agent is a targeted anti-cancer agent. In certain aspects, the targeted anti-cancer agent is selected from the group consisting of Crizotinib, Rapamycin, Erlotinib, Gefinitib, Imatinib, Dasatinib, Sorafenib, Trametinib, and Vorinostat. In certain aspects, the targeted anti-cancer agent is Trametinib. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of ERBB1 and ERBB2. In certain aspects, the methods described herein further comprise having determined from a biological sample derived from the cancer, that the cancer harbors a mutation in at least one gene selected from the group consisting of ERBB1 and ERBB2. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in at least one gene is performed by sequencing the nucleic acid sample. In certain aspects, the cancer in the canine subject is selected from the group consisting of solid tumor, leukemia, lymphocytic leukemia, lymphoma, sarcoma, multiple myeloma, hemangiosarcoma, histiocytic sarcoma, lymphosarcoma, osteosarcoma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer, thyroid cancer and transitional cell carcinoma. In certain aspects, the cancer is transitional cell carcinoma. In certain embodiments, described herein are pharmaceutical compositions formulated for oral administration, comprising Lapatinib, wherein the Lapatinib is present at a concentration of 0.001 mg/mL-100.0 mg/mL.

In certain embodiments, described herein are methods of treating cancer in a canine subject comprising, administering to a subject in need thereof a therapeutically effective amount of a pharmaceutical composition comprising Trametinib. In certain aspects, the Trametinib is administered at a dose equal to or less than 0.05 mg/kg/day. In certain aspects, the Trametinib is administered at a dose of 0.02 mg/kg/day. In certain aspects, the pharmaceutical composition is administered at a frequency selected from the group consisting of twice daily, once daily, once every other day, once every third day, once every fourth day, once every $5^{th}$ day, or weekly. In certain aspects, the Trametinib is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetbolite, topoisomerase inhibitor and a DNA intercalating agent. In certain aspects, at least one additional anti-cancer agent is a targeted anti-cancer agent. In certain aspects, the targeted anti-cancer agent is selected from the group consisting of. Crizotinib, Rapamycin, Erlotinib, Gefinitib, Imatinib, Dasatinib, Sorafenib, Lapatinib, and Vorinostat. In certain aspects, the targeted anti-cancer agent is Rapamycin. In certain aspects, the targeted anti-cancer agent is Dasatinib. In certain aspects, the targeted anti-cancer agent is Lapatinib. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of MEK1 and MEK2. In certain aspects, the methods described herein further comprise having determined from a biological sample derived from the cancer, that the cancer harbors a mutation in at least one gene selected from the group consisting of MEK1 and MEK2. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in the at least one gene is performed by sequencing the nucleic acid sample. In certain aspects, the cancer in the canine subject is selected from the group consisting of: solid tumor, leukemia, lymphocytic leukemia, lymphoma, multiple myeloma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer, thyroid cancer, gingiva carcinoma, and sarcoma (including: soft tissue sarcoma, splenic stromal sarcoma and spindle cell sarcoma, hemangiosarcoma, histiocytic sarcoma, leiomyosarcoma, lymphosarcoma and osteosarcoma). In certain embodiments, described herein are pharmaceutical compositions formulated for oral administration, comprising Trametinib, wherein the Trametinib is present at a concentration of 0.001 mg/mL-100.0 mg/mL.

In certain embodiments, described herein are methods of treating cancer in a canine subject comprising, administering to a subject in need thereof a therapeutically effective amount of a pharmaceutical composition comprising Vorinostat. In certain aspects, the Vorinostat is administered at a dose equal to or less than 100 mg/kg. In certain aspects, the Vorinostat is administered at a dose of 30-60 mg/kg. In certain aspects, the pharmaceutical composition is administered at a frequency selected from the group consisting of twice daily, once daily, once every other day, once every third day, once every fourth day, once every $5^{th}$ day, or weekly. In certain aspects, the Vorinostat is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetabolite, topoisomerase inhibitor and a DNA intercalating agent. In certain aspects, at least one additional anti-cancer agent is a targeted anti-cancer agent. In certain aspects, the targeted anti-cancer agent is selected from the group consisting of. Crizotinib, Rapamycin, Erlotinib, Gefinitib, Imatinib, Dasatinib, Sorafenib, Lapatinib, and Trametinib. In certain aspects, the targeted anti-cancer agent is Rapamycin. In certain aspects, the targeted anti-cancer agent is Trametinib. In certain aspects, the targeted anti-cancer agent is Lapatinib. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of p300, CBP, TIF-2, RAR, BCL-6, AML1, STAT5 and HDAC1. In certain aspects, the methods described herein further comprise having determined from a biological sample derived from the cancer, that the cancer harbors a mutation in at least one gene selected from the group consisting of p300, CBP, TIF-2, RAR, BCL-6, AML1, STAT5 and HDAC1. In certain aspects, the methods described herein further comprise having determined from a biological sample derived from the cancer, that the cancer overexpresses MYC. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in at least one gene is performed by sequencing the nucleic acid sample. In certain aspects, the cancer in the canine subject is selected from the group consisting of solid tumor, leukemia, lymphocytic leukemia, lymphoma, multiple myeloma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer, thyroid cancer, gingiva carcinoma, and sarcoma (including: soft tissue sarcoma, splenic stromal sarcoma and spindle cell sarcoma, hemangiosarcoma, histiocytic sarcoma, leiomyosarcoma, lymphosarcoma and osteosarcoma). In certain aspects, the cancer is hemangiosarcoma. In certain aspects, the cancer is histiocytic sarcoma. In certain embodiments, described herein are pharmaceutical compositions formulated for oral administration, comprising Vorinostat, wherein the Vorinostat is present at a concentration of 0.01 mg/mL-500.0 mg/mL.

In certain embodiments, described herein are methods of treating cancer in a canine subject comprising, administering to a subject in need thereof a therapeutically effective amount of a pharmaceutical composition comprising Imatinib. In certain aspects, the Imatinib is administered at a dose equal to or less than 50 mg/kg. In certain aspects, the Imatinib is administered at a dose of 10 mg/kg. In certain aspects, the pharmaceutical composition is administered at a frequency selected from the group consisting of twice daily, once daily, once every other day, once every third day, once every fourth day, once every $5^{th}$ day, or weekly. In certain aspects, the Imatinib is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetabolite, topoisomerase inhibitor and a DNA intercalating agent. In certain aspects, the at least one additional anti-cancer agent is a targeted anti-cancer agent. In certain aspects, the targeted anti-cancer agent is selected from the group consisting of Crizotinib, Rapamycin, Erlotinib, Gefinitib, Lapatinib, Dasatinib, Sorafenib, Trametinib, and Vorinostat. In certain aspects, the targeted anti-cancer agent is Trametinib. In certain aspects, the targeted anti-cancer agent is Rapamycin. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of ABL, BCR-ABL, PDGFR, and C-KIT. In certain aspects, the methods described herein further comprise having determined from a biological sample derived from the cancer, that the cancer harbors a mutation in at least one gene selected from the group consisting of ABL, BCR-ABL, PDGFR, and C-KIT. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in at least one gene is performed by sequencing the nucleic acid sample. In certain aspects, the cancer in the canine subject is selected from the group consisting of: solid tumor, leukemia, lymphocytic leukemia, lymphoma, sarcoma, multiple myeloma, hemangiosarcoma, histiocytic sarcoma, lymphosarcoma, osteosarcoma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer, thyroid cancer and transitional cell carcinoma. In certain aspects, the cancer is hemangiosarcoma. In certain aspects, the cancer is mast cell tumors. In certain embodiments, described herein are pharmaceutical compositions formulated for oral administration, comprising Imatinib, wherein the Imatinib is present at a concentration of 0.01 mg/mL-100.0 mg/mL.

In certain embodiments, described herein are methods of treating cancer in a canine subject comprising, administering to a subject in need thereof a therapeutically effective amount of a pharmaceutical composition comprising Crizotinib. In certain aspects, Crizotinib is administered at a dose equal to or less than 10 mg/kg. In certain aspects, Crizotinib is administered at a dose of 1 mg/kg-2 mg/kg. In certain aspects, the pharmaceutical composition is administered at a frequency selected from the group consisting of twice daily, once daily, once every other day, once every third day, once every fourth day, once every $5^{th}$ day, or weekly. In certain aspects, Crizotinib is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetabolite, topoisomerase inhibitor and a DNA intercalating agent. In certain aspects, at least one additional anti-cancer agent is a targeted anti-cancer agent. In certain aspects, the targeted anti-cancer agent is selected from the group consisting of Imatinib, Rapamycin, Erlotinib, Gefinitib, Lapatinib, Dasatinib, Sorafenib, Trametinib, and Vorinostat. In certain aspects, the targeted anti-cancer agent is Trametinib. In certain aspects, the targeted anti-cancer agent is Imatinib. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of ALK, c-MET and ROS1. In certain aspects, the methods described herein further comprise having determined from a biological sample derived from the cancer, that the cancer harbors a mutation in at least one gene selected from the group consisting of ALK, c-MET and ROS1. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in at least one gene is performed by sequencing the nucleic acid sample. In certain aspects, the cancer in the canine subject is selected from the group consisting of solid tumor, leukemia, lymphocytic leukemia, lymphoma, sarcoma, multiple myeloma, hemangiosarcoma, histiocytic sarcoma, lymphosarcoma, osteosarcoma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer, thyroid cancer and transitional cell carcinoma. In certain aspects, the cancer is hemangiosarcoma. In certain aspects, the cancer is osteosarcoma. In certain embodiments, described herein are pharmaceutical compositions formulated for oral administration, comprising Crizotinib, wherein Crizotinib is present at a concentration of 0.01 mg/mL-100.0 mg/mL.

In certain embodiments, described herein are methods of treating cancer in a canine subject comprising, administering to a subject in need thereof a therapeutically effective amount of a pharmaceutical composition comprising Sorafenib. In certain aspects, the Sorafenib is administered at a dose of less than 10 mg/kg. In certain aspects, the Sorafenib is administered at a dose of 1 mg/kg-3 mg/kg. In certain aspects, the pharmaceutical composition is administered at a frequency selected from the group consisting of twice daily, once daily, once every other day, once every third day, once every fourth day, once every $5^{th}$ day, or weekly. In certain aspects, the Sorafenib is administered orally. In certain aspects, the methods described herein further comprise administering a therapeutically effective amount of at least one additional anti-cancer agent. In certain aspects, at least one additional anti-cancer agent is a DNA damaging chemotherapeutic agent. In certain aspects, the DNA damaging chemotherapeutic agent is selected from the group consisting of a DNA-alkylating agent, DNA crosslinking agent, antimetabolite, topoisomerase inhibitor and a DNA intercalating agent. In certain aspects, at least one additional anti-cancer agent is a targeted anti-cancer agent. In certain aspects, the targeted anti-cancer agent is selected from the group consisting of: Imatinib, Rapamycin, Erlotinib, Gefinitib, Lapatinib, Dasatinib, Crizontinib, Trametinib, and Vorinostat. In certain aspects, the targeted anti-cancer agent is Imatinib. In certain aspects, the methods described herein further comprise performing surgery on the subject. In certain aspects, the methods described herein further comprise administering to the subject ionizing radiation. In certain aspects, the cancer harbors at least one mutation in at least one gene selected from the group consisting of RAF, c-Kit, FLT-3, RET, VEGFRs and PDG-FRB. In certain aspects, the methods described herein further comprise having determined from a biological sample derived from the cancer, that the cancer harbors a mutation in at least one gene selected from the group consisting of RAF, c-Kit, FLT-3, RET, VEGFRs and PDGFRB. In certain aspects, the biological sample is a nucleic acid sample. In certain aspects, the biological sample is a purified nucleic acid sample. In certain aspects, the sample is DNA. In certain aspects, the sample is RNA. In certain aspects, the determining of the mutation in at least one gene is performed by sequencing the nucleic acid sample. In certain aspects, the cancer in the canine subject is selected from the group consisting of solid tumor, leukemia, lymphocytic leukemia, lymphoma, sarcoma, multiple myeloma, hemangiosarcoma, histiocytic sarcoma, lymphosarcoma, osteosarcoma, transitional cell carcinoma, squamous cell carcinoma, mammary carcinoma, melanoma, mast cell tumors, lipoma, anal gland adenocarcinoma, lung cancer, pancreatic cancer, stomach cancer, prostate cancer, nasal cancer, liver cancer, brain cancer, bladder cancer, thyroid cancer and transitional cell carcinoma. In certain aspects, the cancer is mast cell tumor. In certain aspects, the cancer is osteosarcoma. In certain embodiments, described herein are pharmaceutical compositions formulated for oral administration, comprising Sorafenib, wherein the Sorafenib is present at a concentration of 0.01 mg/mL-100.0 mg/mL.

In certain aspects of the methods described herein, the cancer harbors at least one mutation in at least one gene shown in Tables 1, 2 and 12-26. In certain embodiments, the methods further comprise determining or having determined from a biological sample derived from the cancer, at least one mutation in at least one gene shown in Tables 1, 2, and 12-26.

In certain aspects of the methods described herein, the cancer has increased or decreased expression in at least one gene shown in Tables 1, 2 and 12-26 compared to non-cancerous tissue. In certain embodiments, the methods further comprise determining or having determined from a biological sample derived from the cancer, increased or decreased expression in at least one gene shown in Tables 1, 2, and 12-26 compared to non-cancerous tissue.

BRIEF DESCRIPTION OF THE SEVERAL VIEWS OF THE DRAWINGS

These and other features, aspects, and advantages of the present invention will become better understood with regard to the following description, and accompanying drawings, where.

DETAILED DESCRIPTION

Figure 1:
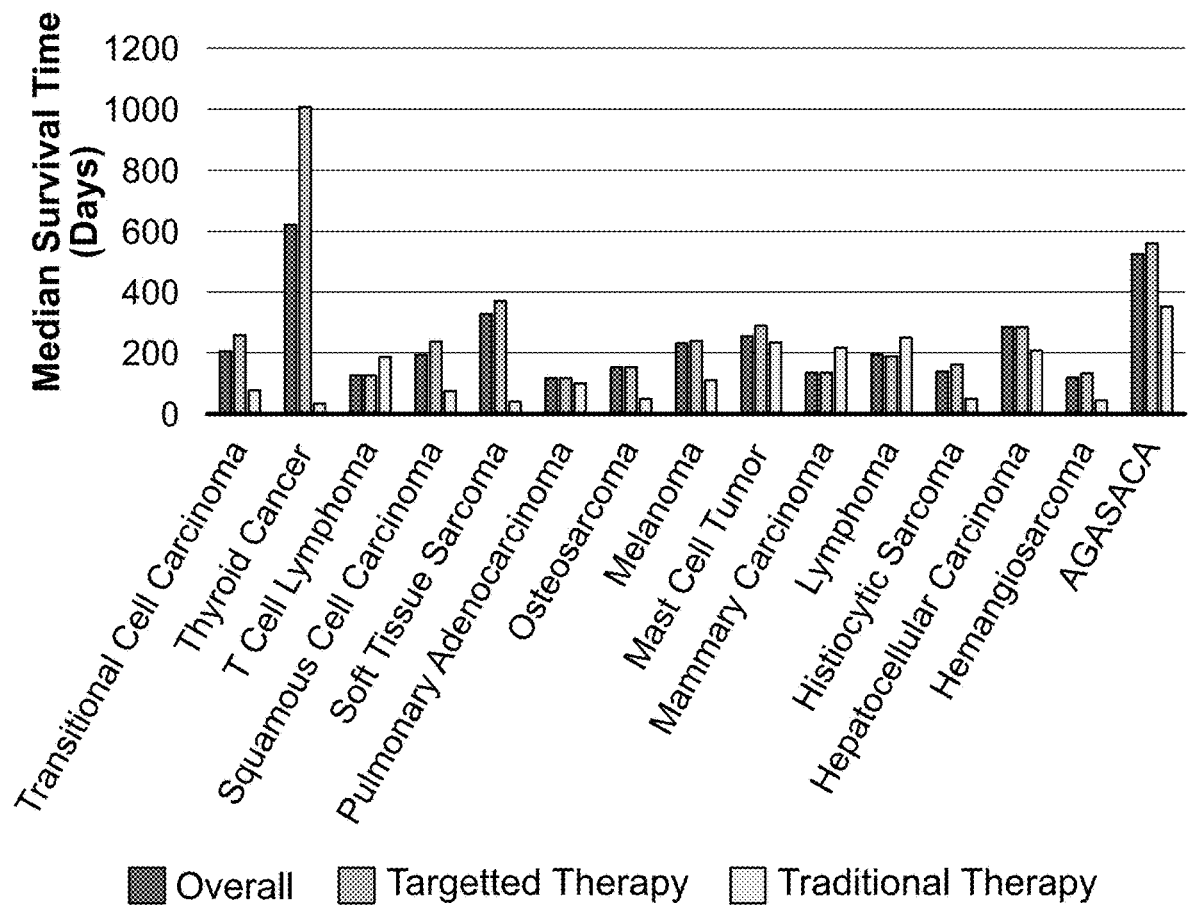
FIG. 1: is a graph showing the median survival of subjects treated with targeted therapies comprising, HDAC inhibitors, Rapamycin, Dasatinib, Lapatinib, Trametinib, Vorinostat, Imatinib, Crizotinib, Sorafenib, and combinations thereof according to the present disclosure versus subjects treated with traditional non-targeted therapies.
Figure 2:
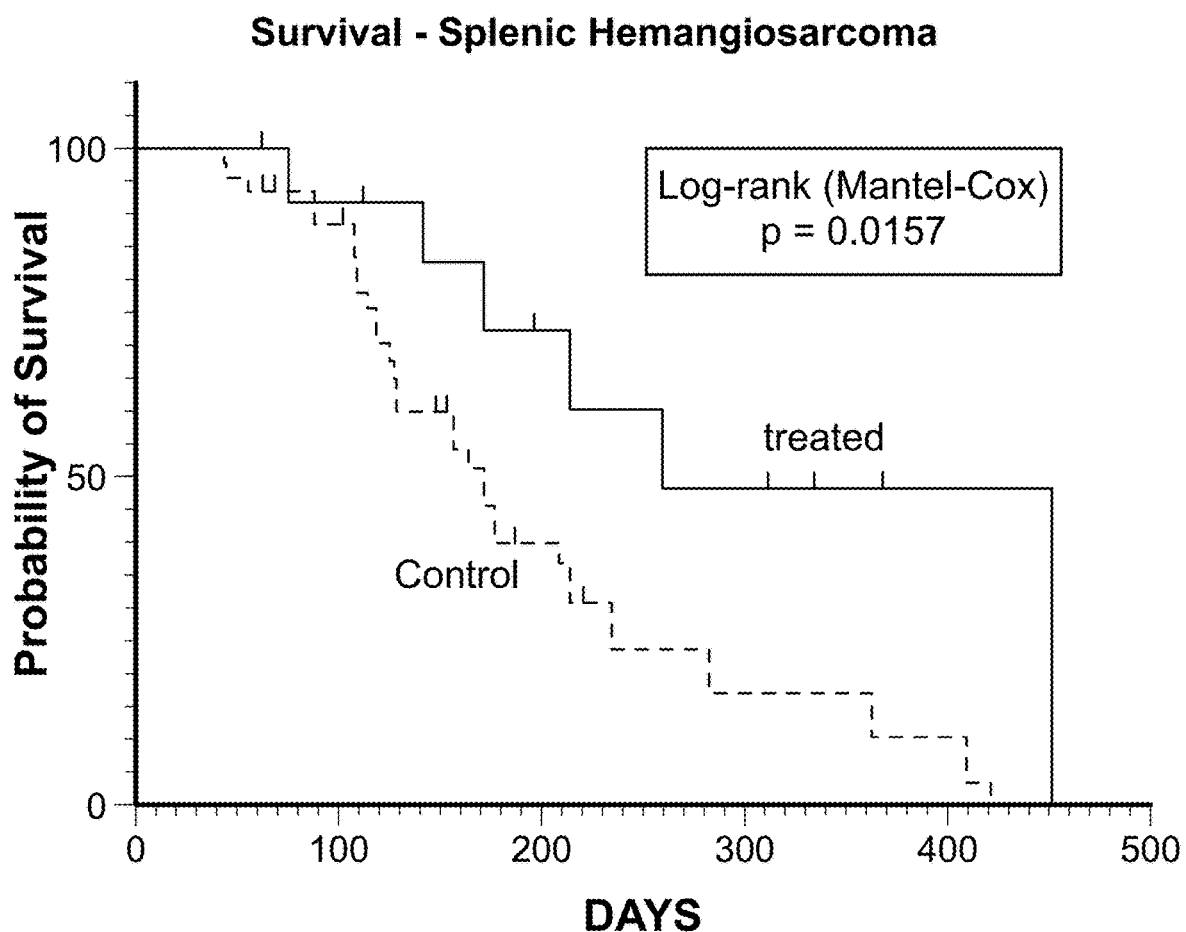
FIG. 2 is a graph showing Kaplan-Meier survival of canine subjects with splenic hemangiosarcoma that have been either treated with chemotherapy and splenectomy alone ("control") or treated with targeted therapy and chemotherapy and splenectomy ("treated").
Figure 3:
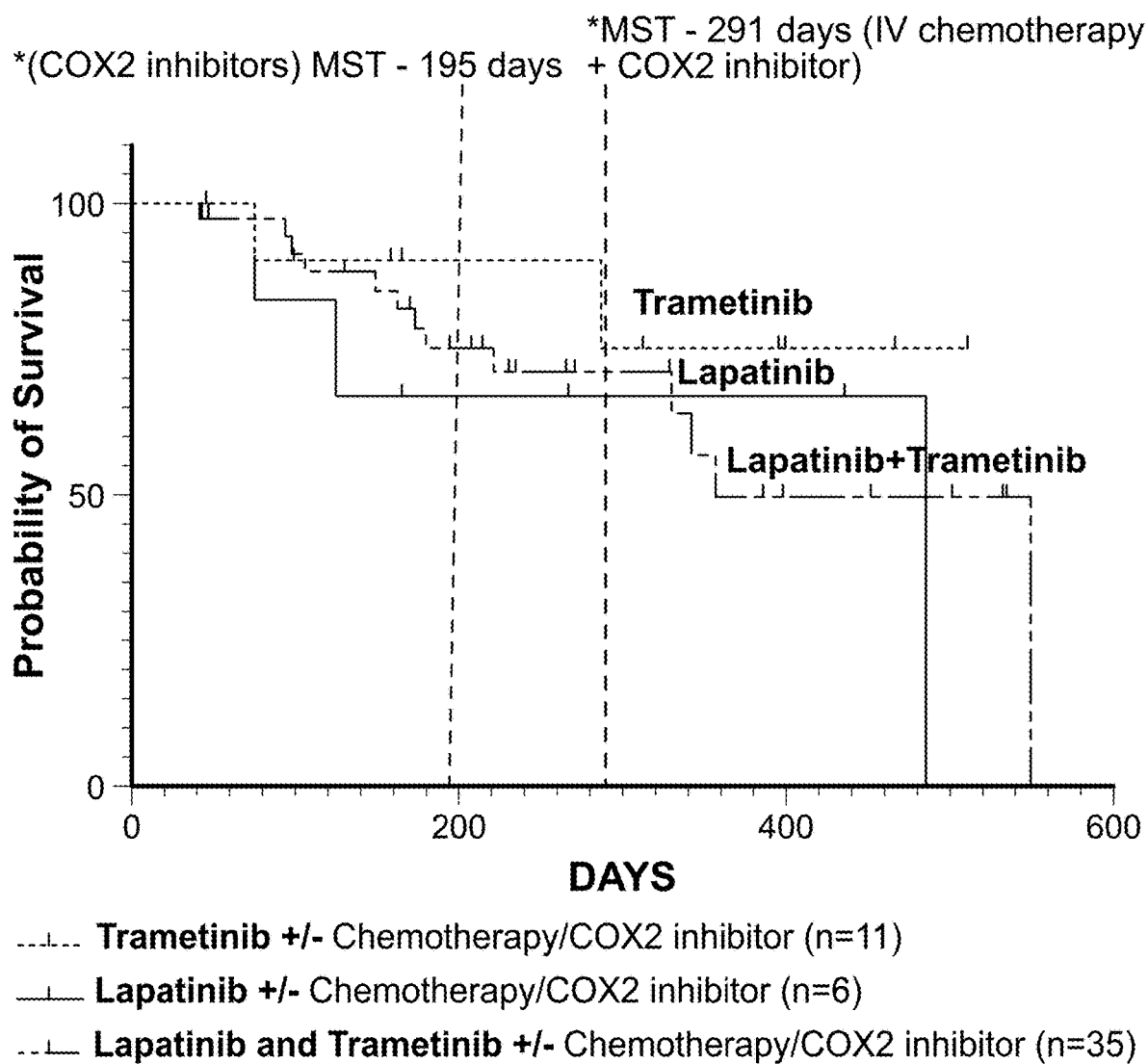
FIG. 3 is a graph showing Kaplan-Meier survival of canine subjects with Transitional Cell Carcinoma (TCC) and/or Urinary Cancer (UC) harboring a BRAF mutation. Dogs treated with targeted drugs (Trametinib, Lapatinib or Lapatinib and Trametinib) with or without standard chemotherapy and a COX2 inhibitor exceeded published median survival times (MST) for either Cox inhibitor treatment alone (195 days) or chemotherapy and Cox2 inhibitor treatment (291 days).
Figure 4:
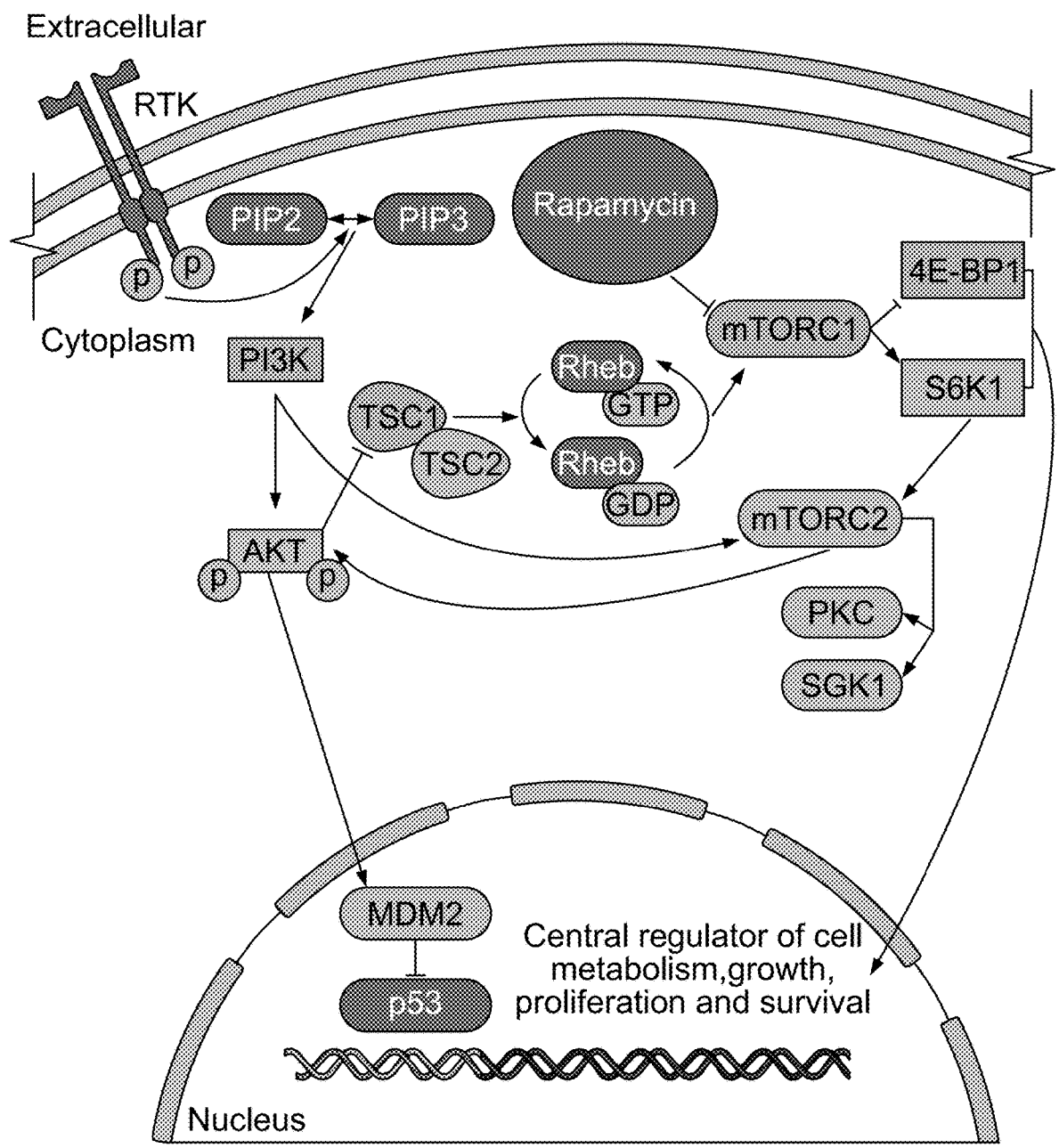
FIG. 4 is an illustration of mechanisms of Rapamycin action in cancer cell signaling. Rapamycin binds to mTORC1 and acts both upstream and downstream of AKT. S6K1 and 4E-BP1 are two well characterized substrates phosphorylated by mTORC1 implicated in transcription, translation, protein, lipids synthesis and is found to be critical for cell growth and metabolism.
Figure 5:
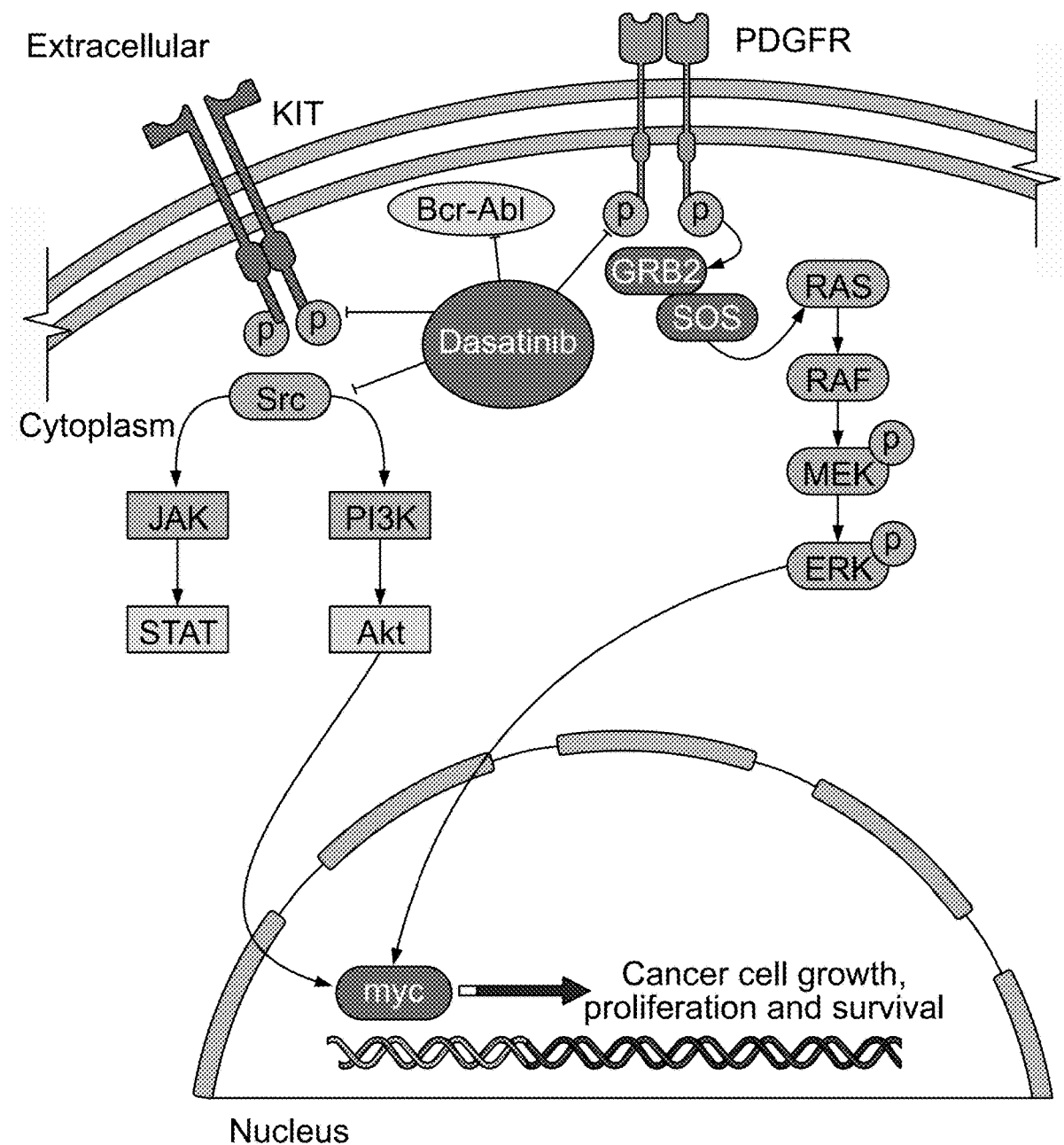
FIG. 5: is an illustration of mechanisms of Dasatinib action in cancer cell signaling. Dasatinib has binding activity to a highly conserved ATP binding site to lock the tyrosine kinase in an inactive state. Dasatinib inhibits SRC family kinases, BCR-ABL, KIT, and PDGFR that play important roles in regulating mitotic events and activating JAK-STAT, PI3K/AKT and MEK/ERK signaling pathways that are critical to tumor cells' proliferation and survival.
Figure 6:
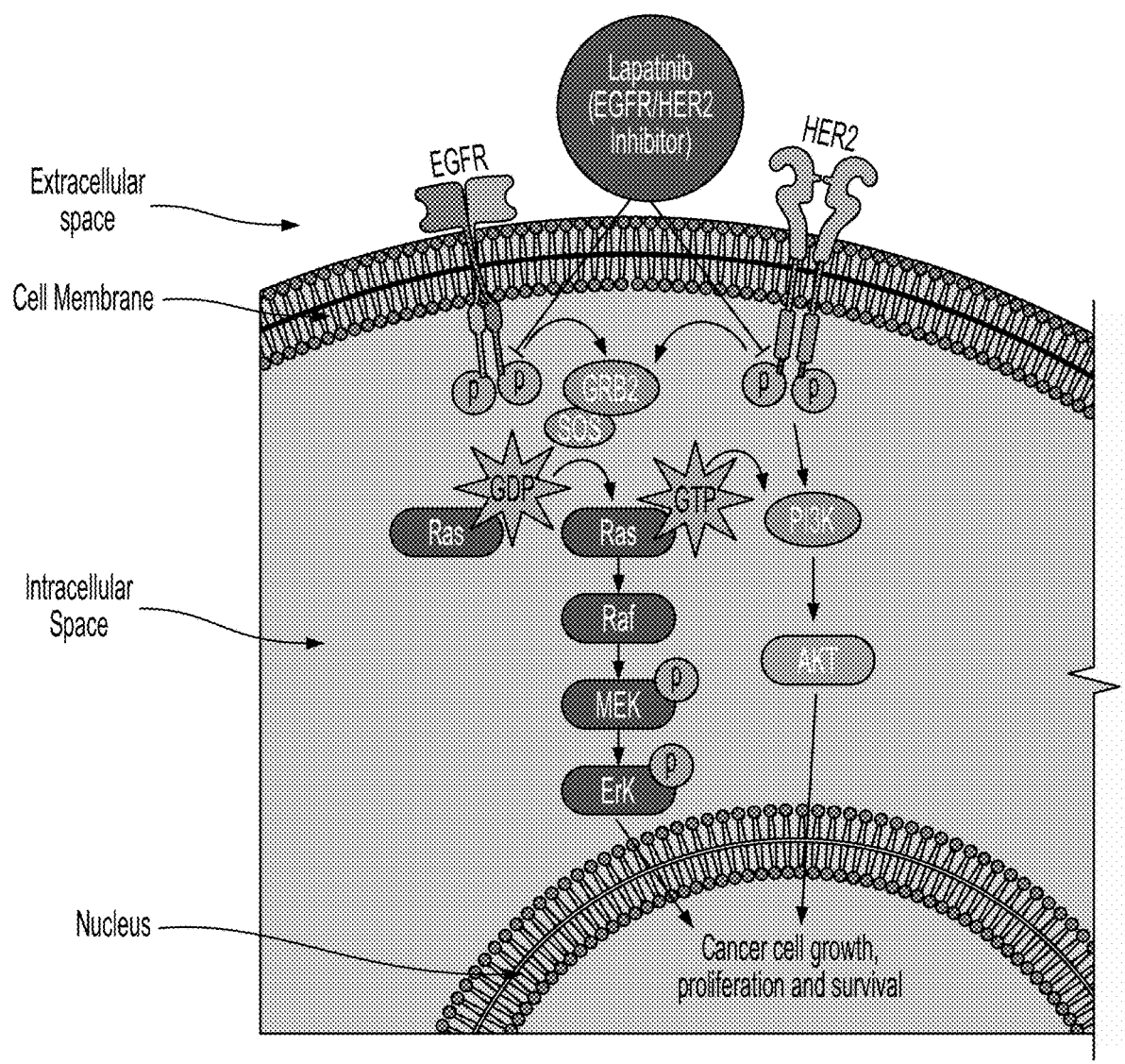
FIG. 6: is an illustration of mechanisms of Lapatinib action in cancer cell signaling. Lapatinib is able to prevent auto-phosphorylation of these receptor tyrosine kinases (e.g., EGFR and HER2), thereby negating downstream signaling cascades. Of particular importance, are the MEK/ERK and PI3K/AKT pathways that enhance the proliferation and survival of cancer cells.
Figure 7:
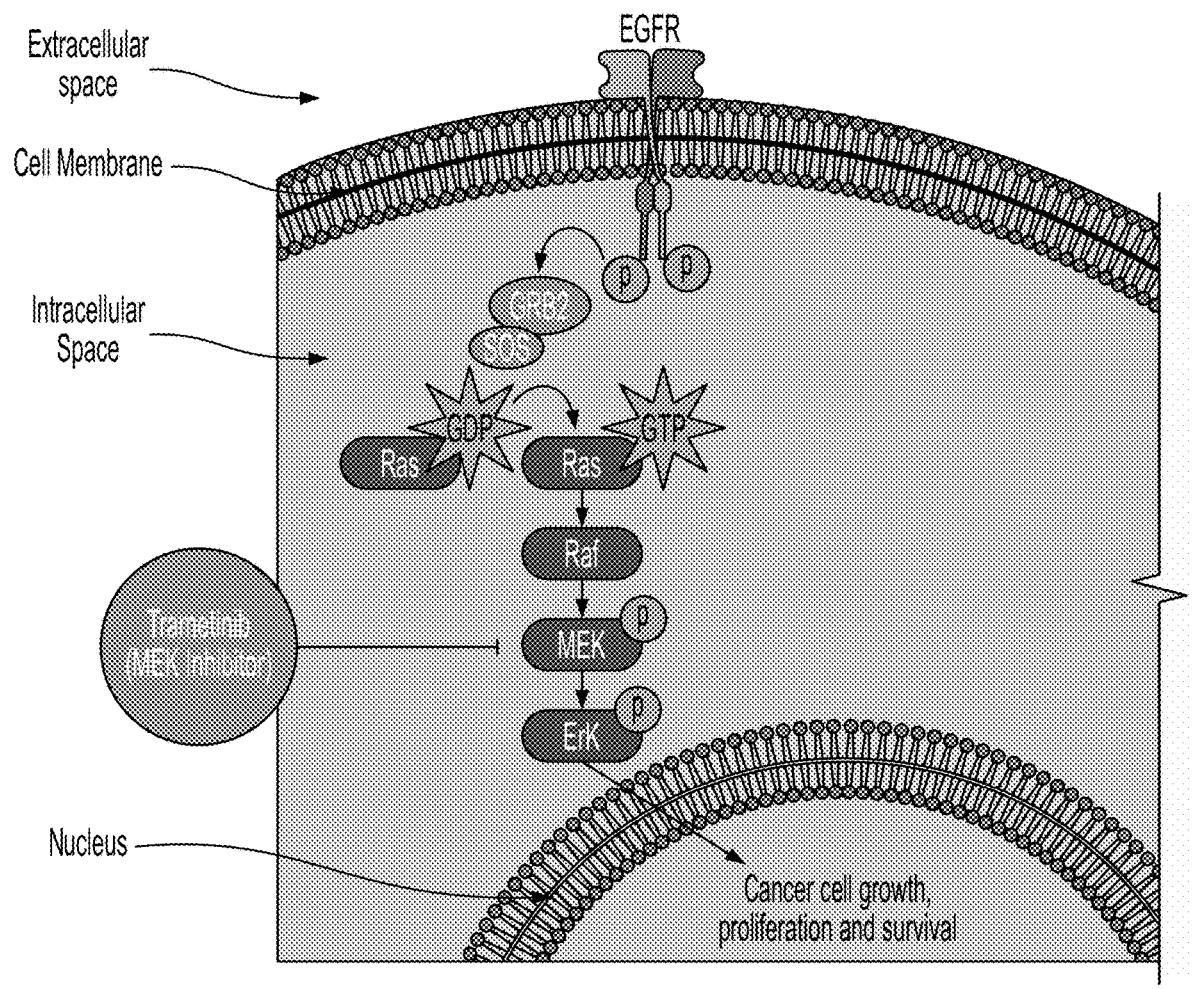
FIG. 7: is an illustration of mechanisms of Trametinib action in cancer cell signaling. Trametinib inhibits, MEK, a component of the MAP kinase cascade, that is activated by upstream receptor tyrosine kinases. Depicted here is the epidermal growth factor receptor, but multiple upstream regulators can activate MEK signaling in the same cell. RAS and RAF proto-oncogenes lie proximally in the cascade but even cancers without activated forms of these oncogenes can have constitutive MEK activation.
Figure 8:
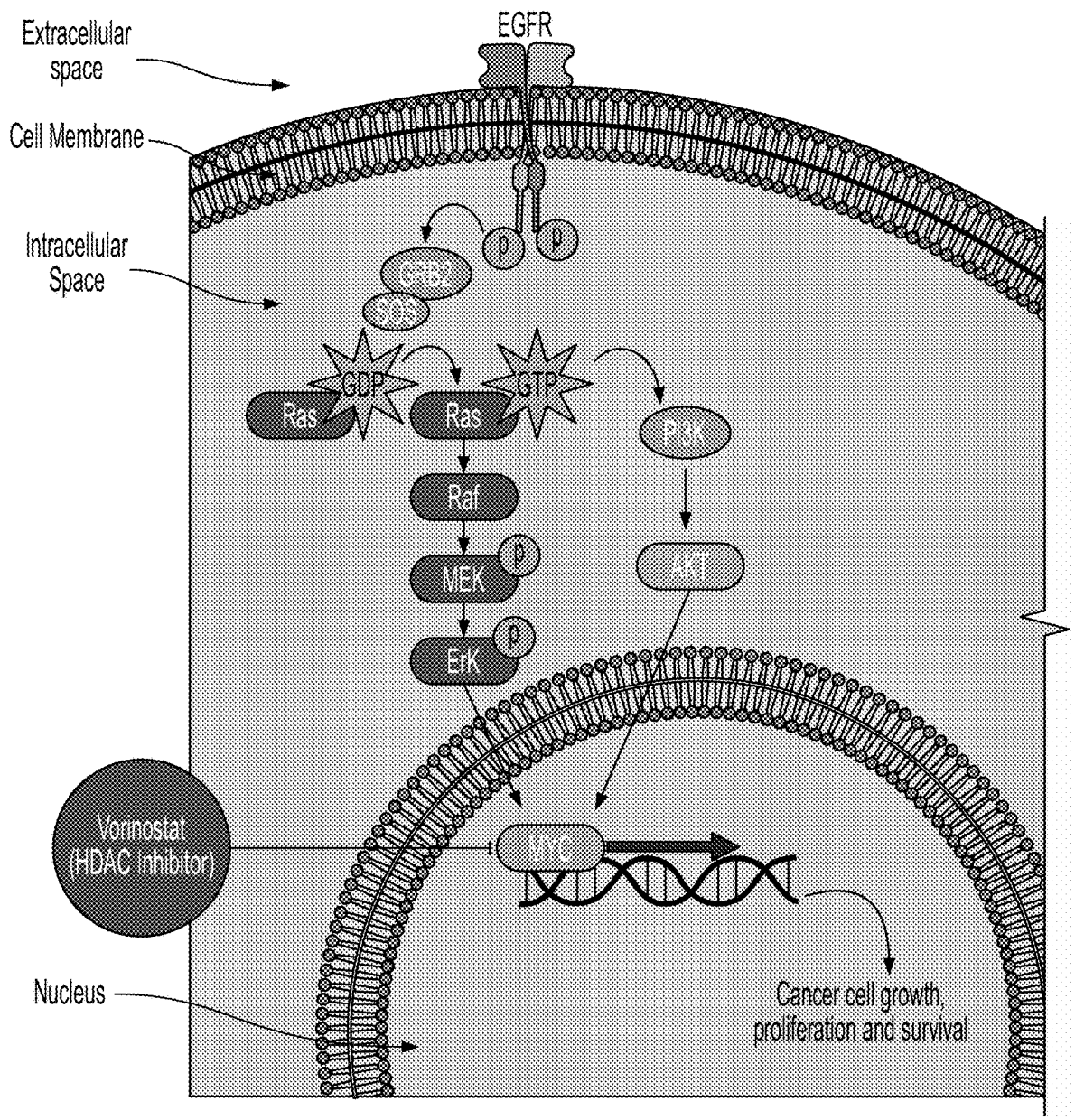
FIG. 8: is an illustration of mechanisms of Vorinostat action in cancer cell signaling. Vorinostat inhibits hyperacetylation of histone proteins leading to cell cycle arrest of cancer cells with activated MEK/ERK and/or PI3K/AKT pathways. Vorinostat is recommended in tumors with MYC overexpression due to the regulatory effects on HDACs.
Figure 9:
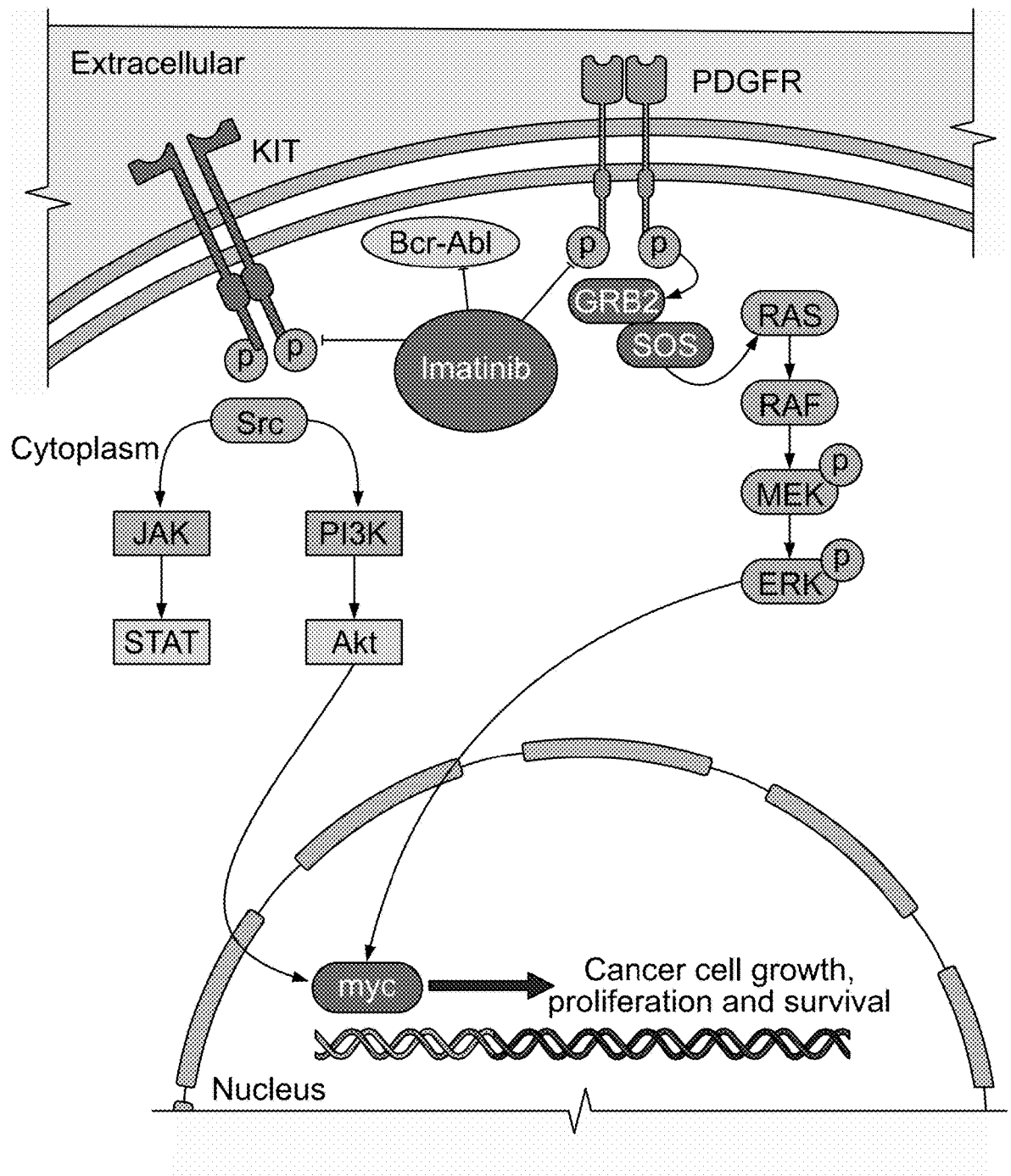
FIG. 9: is an illustration of mechanisms of Imatinib action in cancer cell signaling. Imatinib is able to prevent auto-phosphorylation of KIT, and PDGFR receptor tyrosine kinases, and Bcr-Abl non-receptor tyrosine kinase, thereby negating downstream signaling cascades. Of particular importance, are the MEK/ERK and PI3K/AKT pathways that enhance the proliferation and survival of cancer cells.
Figure 10:
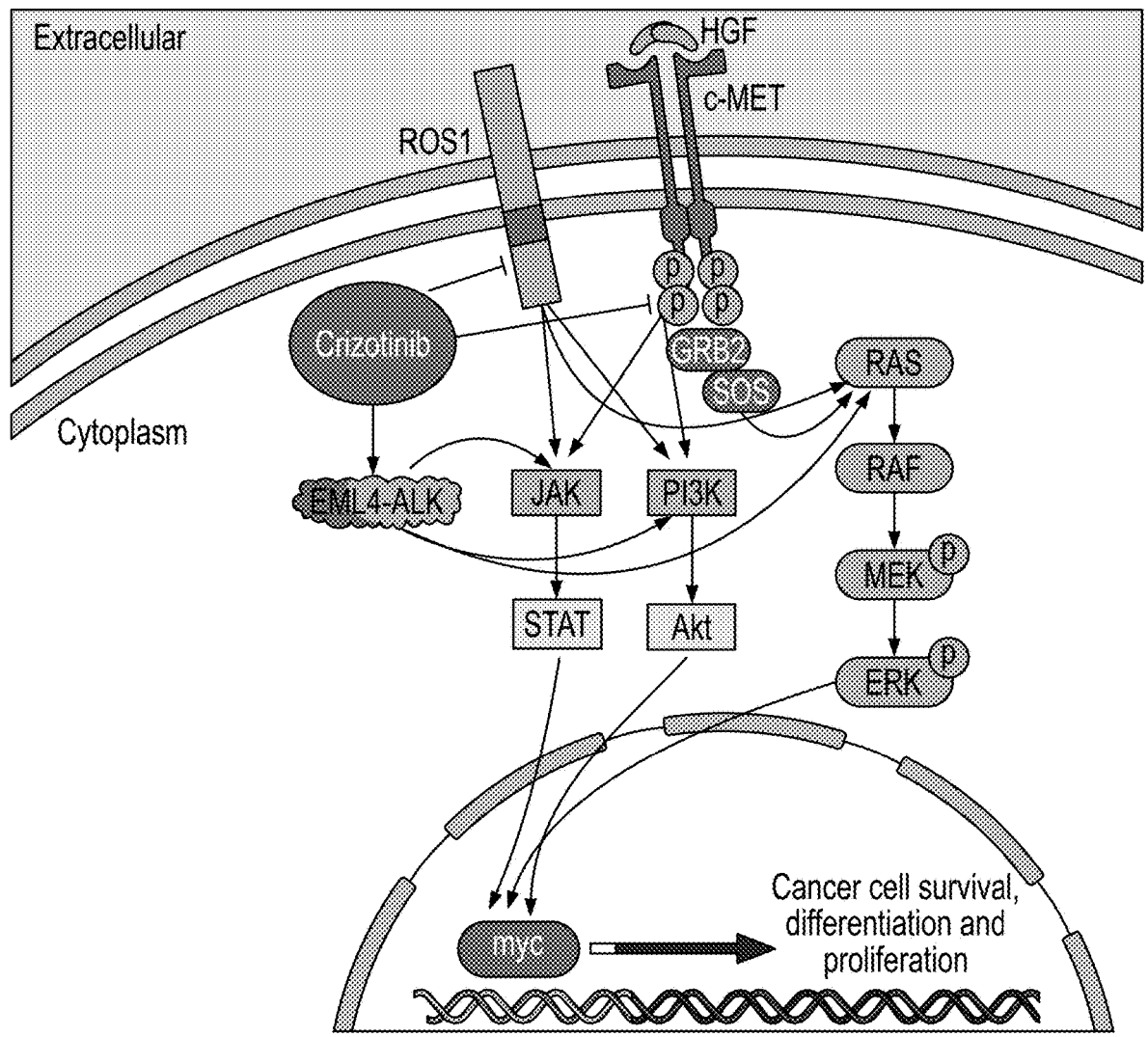
FIG. 10: is an illustration of mechanisms of Crizotinib action in cancer cell signaling. Crizotinib acts on ATP-binding site of ALK-EML4 fusion protein and ROS1. Pathways downstream ALK and ROS1 include: PI3K/AKT/, JAK/STAT and MEK/ERK that promote proliferation and cell survival. Crizotinib inhibits c-MET activation avoiding the phosphorylation of adaptor proteins such as GRB2, GAB1, SRC, ShC and c-CBL and subsequent inhibition of activation of PI3K, AKT, STAT and ERK.
Figure 11:
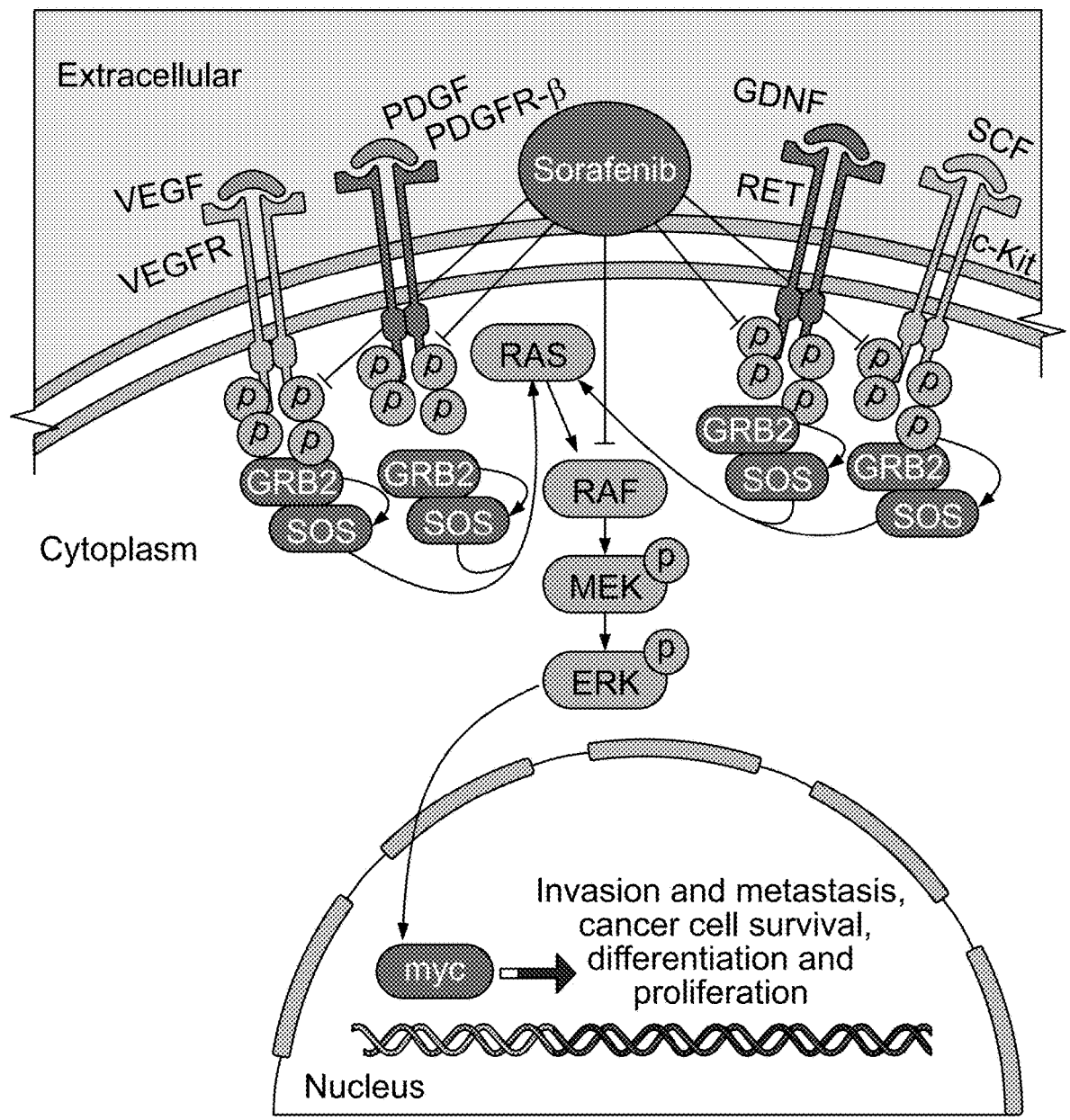
FIG. 11: is an illustration of mechanisms of Sorafenib action in cancer cell signaling. Sorafenib blocks receptor tyrosine kinase signaling (VEGFR, PDGFR-β, c-KIT and RET) and inhibits downstream Raf serine/threonine kinases (ARAF, BRAF, mutant BRAF V600E and CRAF) activity to prevent tumor growth by anti-angiogenic, antiproliferative and pro-apoptotic effects.

Briefly, and as described in more detail below, described herein are methods useful for the treatment of cancer in a canine subject with a pharmaceutical compositions comprising HDAC inhibitors, Rapamycin, Dasatinib, Lapatinib, Trametinib, Vorinostat, Imatinib, Crizotinib, Sorafenib, and combinations thereof. Also described herein are methods for identification or selection of subjects with cancers that are likely to derive significant therapeutic responses to administration of the pharmaceutical compositions comprising HDAC inhibitors, Rapamycin, Dasatinib, Lapatinib, Trametinib, Vorinostat, Imatinib, Crizotinib, Sorafenib, and combinations thereof. The methods of the present disclosure are useful for treating subjects with cancer with targeted therapies comprising HDAC inhibitors, Rapamycin, Dasatinib, Lapatinib, Trametinib, Vorinostat, Imatinib, Crizotinib, Sorafenib, and combinations thereof for increasing survival of the subjects compared to traditional therapies (FIG. 1 and Table 1). In certain aspects, the methods herein cause increased survival of a subject with cancer following treatment with the targeted therapies disclosed herein compared to traditional chemotherapy (FIGS. 2 and 3).

Definitions

Terms used in the claims and specification are defined as set forth below unless otherwise specified.

The term "canine cancer" can refer to any cancer, tumor or hyperproliferative disorder that is present in a canine subject. In embodiments, the canine cancer is a specified cancer that is surprisingly responsive to one or more of the treatments described in this disclosure.

The term "treating" refers to any therapeutically beneficial result in the treatment of a disease state, e.g., a cancer disease state, including lessening in the severity or progression, remission, or cure thereof.

The term "sufficient amount" means an amount sufficient to produce a desired effect, e.g., an amount sufficient to modulate protein aggregation in a cell.

The term "therapeutically effective amount" is an amount that is effective to ameliorate a symptom of cancer or hyperproliferative disease.

The term "anti-cancer agent" refers to, but is not limited to chemotherapeutic agents, targeted therapies, hormones, and immunotherapies. Anti-cancer agents can be, but are not limited to, a small molecule, an antibody or antibody fragment, nucleic acid (e.g., DNA or RNA), carbohydrates, peptides, lipids, exosomes, cells, or combinations thereof.

The term "targeted anti-cancer agent" refers to, but is not limited to, anti-cancer agents that specifically alter a cancer cell characteristic (e.g., an agent that interacts with a gene product, such as a protein or RNA, that regulates a cancer cell characteristic, such as cell proliferation, cell survival, metastasis, immune evasion, etc.).

The term "overexpression" when referring to a gene (e.g., an oncogene such as MYC), refers to increased amounts of mRNA or protein with respect to a non-cancer tissue control sample. A gene can be considered overexpressed when the mRNA and/or protein amounts of the gene are greater than 2.0 fold, 5 fold, 10 fold, 20 fold, 30 fold, 40 fold, 50 fold, 60 fold, 70 fold, 80 fold, 90 fold, 100 fold, 150 fold, 200 fold 300 fold, 400 fold 500 fold or 1000 fold the amount of RNA and/or protein of anon-cancer tissue control sample. In certain embodiments, the gene is overexpressed when the mRNA and/or protein amounts of the gene are 2 fold to 10 fold, 5 fold to 10 fold, 10 fold to 100 fold, 10 fold to 50 fold, 50 fold to 100 fold, or 100 fold to 1000 fold greater than the amount of RNA and or protein of a non-cancer tissue control sample. Overexpression can be determined by any appropriate method known in the art, including, but not limited to, RNA SEQ, and quantitative PCR, immunohistochemistry.

The term "underexpression" when referring to a gene (e.g., a tumor suppressor gene such as p53), refers to decreased amounts of mRNA or protein with respect to a non-cancer tissue control sample. A gene can be considered underexpressed when the mRNA and/or protein amounts of the gene are less than 2.0 fold, 5 fold, 10 fold, 20 fold, 30 fold, 40 fold, 50 fold, 60 fold, 70 fold, 80 fold, 90 fold, 100 fold, 150 fold, 200 fold 300 fold, 400 fold 500 fold or 1000 fold the amount of RNA and/or protein of anon-cancer tissue control sample. In certain embodiments, the gene is underexpressed when the mRNA and/or protein amounts of the gene are 2 fold to 10 fold, 5 fold to 10 fold, 10 fold to 100 fold, 10 fold to 50 fold, 50 fold to 100 fold, or 100 fold to 1000 fold less than the amount of RNA and or protein of a non-cancer tissue control sample. Underexpression can be determined by any appropriate method known in the art, including, but not limited to, RNA SEQ, and quantitative PCR, immunohistochemistry.

Abbreviations used in this application include the following: HDAC (histone deacetylase), ATM, mTOR, PI3K, AKT, Ras, ABL, BCR-ABL, c-KIT, EPHA2, PDGFR, a Src Family Kinase, ERBB1, ERBB2, MEK1, MEK2, p300, CBP, TIF-2, RAR, BCL-6, AML1, STAT5, HDAC1, MYC, ALK, c-MET, ROS1, RAF, FLT-3, RET, VEGFRs and PDGFRB.

ATM is also known as ataxia-telangiectasia mutated (ATM) kinase, Serine-Protein kinase ATM, A-T Mutated, TELL, and Telomere Maintenance 1 Homolog. *Canis lupus*

*familiaris* (canine) PDGFRB is encoded by the gene having an Ensembl identification number of ENSCAFG00000014454.

mTOR is also known as, Mechanistic Target Of Rapamycin Kinase, Mammalian Target Of Rapamycin, Rapamycin And FKBP12 Target 1, FK506-Binding Protein 12-Rapamycin Complex-Associated Protein 1, Mechanistic Target Of Rapamycin (Serine/Threonine Kinase), FK506 Binding Protein 12-Rapamycin Associated Protein 2, FKBP12-Rapamycin Complex-Associated Protein 1, Serine/Threonine-Protein Kinase MTOR, Rapamycin Associated Protein FRAP2, FKBP-Rapamycin Associated Protein, Mechanistic Target Of Rapamycin, Rapamycin Target Protein 1, FRAP1, RAFT1, FRAP, DJ576K7.1 (FK506 Binding Protein 12-Rapamycin Associated Protein 1), FK506 Binding Protein 12-Rapamycin Associated Protein 1, FKBP12-Rapamycin Complex-Associated Protein, Rapamycin Target Protein, EC 2.7.11.1, MTOR, or SKS. *Canis lupus familiaris* (canine) mTOR is encoded by the gene having an Ensembl identification number of: ENSCAFG00000016648.

PI3K refers to the family of kinases also known as Phosphoinositide 3-kinases or phosphatidylinositol 3-kinases.

AKT refers to AKT Serine/Threonine Kinase 1, V-Akt Murine Thymoma Viral Oncogene Homolog 1, RAC-Alpha Serine/Threonine-Protein Kinase, Protein Kinase B Alpha, Proto-Oncogene C-Akt, Protein Kinase B, RAC-PK-Alpha, EC 2.7.11.1, PKB Alpha, PKB, and RAC. *Canis lupus familiaris* (canine) AKT1 is encoded by the gene having an Ensembl identification number of: ENSCAFG00000018354.

ABL is also known as ABL Proto-Oncogene 1, Non-Receptor Tyrosine Kinase, V-Abl Abelson Murine Leukemia Viral Oncogene Homolog 1, C-Abl Oncogene 1, Receptor Tyrosine Kinase, Abelson Tyrosine-Protein Kinase 1, Tyrosine-Protein Kinase ABL1, Proto-Oncogene C-Abl, EC 2.7.10.2, JTK7, and P150. *Canis lupus familiaris* (canine) ABL is encoded by the gene having an Ensembl identification number of ENSCAFG00000019938.

BCR-ABL is also known as BCR-ABL Major-Breakpoint Cluster Region; BCR P210 Philadelphia Chromosome Recombination Region, T(9;22)(Q34;Q11) M-BCR Recombination Region, and BCR P210 Breakpoint Recombination Region.

c-KIT is also known as KIT Proto-Oncogene, Receptor Tyrosine Kinase, V-Kit Hardy-Zuckerman 4 Feline Sarcoma Viral Oncogene Homolog, Mast/Stem Cell Growth Factor Receptor Kit, Tyrosine-Protein Kinase Kit, Piebald Trait Protein, Proto-Oncogene C-Kit, EC 2.7.10.1, P145 C-Kit, SCFR, PBT, V-Kit Hardy-Zuckerman 4 Feline Sarcoma Viral Oncogene-Like, Proto-Oncogene Tyrosine-Protein Kinase Kit, Soluble KIT Variant 1, C-Kit Protooncogene, CD117 Antigen, Piebald Trait, EC 2.7.10, C-Kit, CD117, and MASTC. *Canis lupus familiaris* (canine) c-Kit is encoded by the gene having an Ensembl identification number of ENSCAFG00000002065.

EPHA2 is also known as EPH Receptor A2, Tyrosine-Protein Kinase Receptor ECK, Ephrin Type-A Receptor 2, EC 2.7.10.1, ECK, Epithelial Cell Receptor Protein Tyrosine Kinase, Soluble EPHA2 Variant 1, Epithelial Cell Kinase, EC 2.7.10, CTRCT6, ARCC2, CTPP1, EphA2, and CTPA. *Canis lupus familiaris* (canine) EPHA2 is encoded by the gene having an Ensembl identification number of ENSCAFG00000016011.

PDGFR includes PDGFRA and PDGFRB. PDGFRA is also known as Platelet Derived Growth Factor Receptor Alpha, Platelet-Derived Growth Factor Receptor, Alpha Polypeptide, Alpha-Type Platelet-Derived Growth Factor Receptor, Platelet-Derived Growth Factor Receptor Alpha, Platelet-Derived Growth Factor Receptor 2, CD140 Antigen-Like Family Member A, CD140a Antigen, PDGF-R-Alpha, and EC 2.7.10.1. *Canis lupus familiaris* (canine) PDGFRA is encoded by the gene having an Ensembl identification number of ENSCAFG00000002057. PDGFRB is also known as Platelet Derived Growth Factor Receptor, Beta Platelet-Derived Growth Factor Receptor, Beta Polypeptide, Beta-Type Platelet-Derived Growth Factor Receptor, Platelet-Derived Growth Factor Receptor Beta, Platelet-Derived Growth Factor Receptor 1, CD140 Antigen-Like Family Member B, PDGF-R-Beta, EC 2.7.10.1, PDGFR-Beta, PDGFR-1, PDGFR1, PDGFR, Beta Platelet-Derived Growth Factor Receptor, Activated Tyrosine Kinase PDGFRB•CD140b Antigen, NDEL1-PDGFRB, EC 2.7.10, CD140B, IBGC4, JTK12, PENTT, IMF1, and KOGS. *Canis lupus familiaris* (canine) PDGFRB is encoded by the gene having an Ensembl identification number of ENSCAFG00000018214.

Src Family Kinase refers to non-receptor tyrosine kinases that includes: Src, Yes, Fyn, and Fgr, forming the SrcA subfamily, Lck, Hck, Blk, and Lyn and Frk.

ERBB1 is also referred to as Epidermal Growth Factor Receptor, Receptor Tyrosine-Protein Kinase ErbB-1, Erb-B2 Receptor Tyrosine Kinase 1, Proto-Oncogene C-ErbB-1, EC 2.7.10.1, ERBB1, ERBB, HER1, Epidermal Growth Factor Receptor (Avian Erythroblastic Leukemia Viral (V-Erb-B) Oncogene Homolog), Erythroblastic Leukemia Viral (V-Erb-B) Oncogene Homolog (Avian), Avian Erythroblastic Leukemia Viral (V-Erb-B) Oncogene Homolog, Epidermal Growth Factor Receptor Tyrosine Kinase Domain, Cell Proliferation-Inducing Protein 61, Cell Growth Inhibiting Protein 40, EC 2.7.10, NISBD2, PIG61 and MENA. *Canis lupus familiaris* (canine) ERRB1 is encoded by the gene having an Ensembl identification number of: ENSCAFG00000003465.

ERBB2 is also known as: Erb-B2 Receptor Tyrosine Kinase 2, V-Erb-B2 Avian Erythroblastic Leukemia Viral Oncogene Homolog 2, Tyrosine Kinase-Type Cell Surface Receptor HER2, Neuro/Glioblastoma Derived Oncogene Homolog, Human Epidermal Growth Factor Receptor 2, Receptor Tyrosine-Protein Kinase ErbB-2, Metastatic Lymph Node Gene 19 Protein, Proto-Oncogene C-ErbB-2, Proto-Oncogene Neu, EC 2.7.10.1, P185erbB2, MLN 19, HER2, NGL, NEU, V-Erb-B2 Avian Erythroblastic Leukemia Viral Oncogene Homolog 2 (Neuro/Glioblastoma Derived Oncogene Homolog), V-Erb-B2 Erythroblastic Leukemia Viral Oncogene Homolog 2, Neuro/Glioblastoma Derived Oncogene Homolog, V-Erb-B2 Avian Erythroblastic Leukemia Viral Oncoprotein 2, Neuroblastoma/Glioblastoma Derived Oncogene Homolog, C-Erb B2/Neu Protein, CD340 Antigen, HER-2/Neu, Herstatin, EC 2.7.10, CD340, HER-2, MLN19, and TKR1. *Canis lupus familiaris* (canine) ERRB2 is encoded by the gene having an Ensembl identification number of ENSCAFG00000016351.

MEK1 is also referred to as Mitogen-Activated Protein Kinase Kinase 1, MAP2K1, Dual Specificity Mitogen-Activated Protein Kinase Kinase 1, ERK Activator Kinase 1, MAPK/ERK Kinase 1, EC 2.7.12.2, MAPKK 1, MKK1 and PRKMK1. *Canis lupus familiaris* (canine) MEK1 is encoded by the gene having an Ensembl identification number of ENSCAFG00000017298.

MEK2 is also known as: Mitogen-Activated Protein Kinase Kinase 2, MAP2K2, Dual Specificity Mitogen-Activated Protein Kinase Kinase 2, ERK Activator Kinase 2, MAP Kinase Kinase 2, MAPK/ERK Kinase 2, EC 2.7.12.2, PRKMK2, MKK2, Mitogen-Activated Protein Kinase Kinase 2, P45, MAPKK 2, and MAPKK2. *Canis lupus familiaris* (canine) MEK2 is encoded by the gene having an Ensembl identification number of: ENSCAFG00000019138.

P300 is also referred to as: E1A Binding Protein P300, Histone Acetyltransferase P300, Protein Propionyltransferase P300, Histone Crotonyltransferase P300, Histone Butyryltransferase P300, E1A-Associated Protein P300, EC 2.3.1.48, P300 HAT, E1A-Binding Protein, 300kD, EC 2.3.1, EC 2.3.1, KAT3B, MKHK2, and RSTS2. *Canis lupus familiaris* (canine) p300 is encoded by the gene having an Ensembl identification number of ENSCAFG00000001125.5

CBP is also referred to as: CREBBP, CREB-Binding Protein, KAT3A, MKHK1, RSTS1, and RSTS. *Canis lupus familiaris* (canine) CBP is encoded by the gene having an Ensembl identification number of ENSCAFG00000019251.

TIF-2 is also referred to as NCOA2, Nuclear Receptor Coactivator 2; Class E Basic Helix-Loop-Helix Protein 75, Transcriptional Intermediary Factor 2, BHLHe75, NCoA-2, SRC2, Glucocorticoid Receptor-Interacting Protein-1, P160 Steroid Receptor Coactivator 2, EC 2.3.1.48, BHLHE75, KAT13C, GRIP1, and HTIF2. *Canis lupus familiaris* (canine) TIF-2 is encoded by the gene having an Ensembl identification number of ENSCAFG00000007775.

RAR is also referred to as: Retinoic Acid Receptor Alpha, RARA, Nuclear Receptor Subfamily 1 Group B Member 1, RAR-Alpha, NR1B1, Nucleophosmin-Retinoic Acid Receptor Alpha Fusion Protein NPM-RAR Long Form, Retinoic Acid Nuclear Receptor Alpha Variant, Retinoic Acid Nuclear Receptor Alpha Variant 2, Retinoic Acid Receptor, Alpha Polypeptide, and Retinoic Acid Receptor, Alpha. *Canis lupus familiaris* (canine) RAR is encoded by the gene having an Ensembl identification number of ENSCAFG00000016060.

BCL-6 is also referred to as: BCL6 Transcription Repressor, Zinc Finger Protein 51, Zinc Finger And BTB Domain-Containing Protein 27, BCL6, Transcription Repressor, B-Cell Lymphoma 6 Protein, B-Cell Lymphoma 5 Protein, B Cell CLL/Lymphoma 6, Protein LAZ, ZBTB27, ZNF51 BCL5, LAZ3, Lymphoma-Associated Zinc Finger Gene On Chromosome 3, Cys-His2 Zinc Finger Transcription Factor, Zinc Finger Transcription Factor BCL6S, B-Cell Lymphoma 6 Protein Transcript, and BCL6A. *Canis lupus familiaris* (canine) BCL-6 is encoded by the gene having an Ensembl identification number of ENSCAFG00000013904.

AML1 is also referred to as RUNX1, RUNX Family Transcription Factor 1, Runt-Related Transcription Factor 1, Runt Related Transcription Factor 1, Polyomavirus Enhancer-Binding Protein 2 Alpha B Subunit, SL3/AKV Core-Binding Factor Alpha B Subunit, SL3-3 Enhancer Factor 1 Alpha B Subunit, Acute Myeloid Leukemia 1 Protein, Oncogene AML-1, PEBP2-Alpha B, PEA2-Alpha B, and CBFA2. *Canis lupus familiaris* (canine) AML1 is encoded by the gene having an Ensembl identification number of ENSCAFG00000009596.

STAT5 is also referred to as STAT5A, Signal Transducer And Activator Of Transcription 5A, Epididymis Secretory Sperm Binding Protein, and MGF. *Canis lupus familiaris* (canine) STAT5 is encoded by the gene having an Ensembl identification number of ENSCAFG00000015346.

HDAC1 is also referred to as Histone Deacetylase 1, EC 3.5.1.98, RPD3L1, HD1, Reduced Potassium Dependency, Yeast Homolog-Like 1, GON-10, KDAC1, and RPD3. *Canis lupus familiaris* (canine) HDAC1 is encoded by the gene having an Ensembl identification number of ENSCAFG00000010597.

MYC is also referred to as MYC Proto-Oncogene, BHLH Transcription Factor, V-Myc Avian Myelocytomatosis Viral Oncogene Homolog, Class E Basic Helix-Loop-Helix Protein 39, Myc Proto-Oncogene Protein, Transcription Factor P64, Proto-Oncogene C-Myc, BHLHe39, Myc-Related Translation/Localization Regulatory Factor, Avian Myelocytomatosis Viral Oncogene Homolog, V-Myc Myelocytomatosis Viral Oncogene Homolog, C-Myc, MRTL, and MYCC. *Canis lupus familiaris* (canine) MYC is encoded by the gene having an Ensembl identification number of ENSCAFG00000001086.

ALK is also referred to as ALK Receptor Tyrosine Kinase, Anaplastic Lymphoma Receptor Tyrosine Kinase, and ALK Tyrosine Kinase Receptor. *Canis lupus familiaris* (canine) ALK is encoded by the gene having an Ensembl identification number ENSCAFG00000005297.

c-MET is also referred to as MET Proto-Oncogene, Receptor Tyrosine Kinase, Hepatocyte Growth Factor Receptor, Tyrosine-Protein Kinase Met, Scatter Factor Receptor, Proto-Oncogene C-Met, HGF/SF Receptor, HGF Receptor, and SF Receptor. *Canis lupus familiaris* (canine) c-MET is encoded by the gene having an Ensembl identification number ENSCAFG00000003406.

ROS1 is also referred to as ROS Proto-Oncogene 1, Receptor Tyrosine Kinase, V-Ros Avian UR2 Sarcoma Virus Oncogene Homolog 1, C-Ros Oncogene 1, Receptor Tyrosine Kinase, Proto-Oncogene Tyrosine-Protein Kinase ROS, and Proto-Oncogene C-Ros-1. *Canis lupus familiaris* (canine) ROS1 is encoded by the gene having an Ensembl identification number ENSCAFG00000000923.

As used herein, the term "VEGFRs" refers to the Vascular Endothelial Growth Factor Receptors, including (VEGFR-1, VEGFR-2, VEGFR-3).

VEGFR-1 is also referred to as Flt-1, Fins Related Tyrosine Kinase 1, Vascular Endothelial Growth Factor Receptor 1, Vascular Permeability Factor Receptor, Fms-Related Tyrosine Kinase 1 (Vascular Endothelial Growth Factor/Vascular Permeability Factor Receptor), Tyrosine-Protein Kinase Receptor FLT, Tyrosine-Protein Kinase FRT, and Fms-Like Tyrosine Kinase 1. *Canis lupus familiaris* (canine) VEGFR-1 is encoded by the gene having an Ensembl identification number ENSCAFG00000006701.

VEGFR-2 is also referred to as KDR, Flk-1, Kinase Insert Domain Receptor, Vascular Endothelial Growth Factor Receptor 2, Kinase Insert Domain Receptor (A Type III Receptor Tyrosine Kinase), Protein-Tyrosine Kinase Receptor Flk-1, Fetal Liver Kinase 1, Soluble VEGFR2•CD309 Antigen, EC 2.7.10, VEGFR-2 or CD309. *Canis lupus familiaris* (canine) VEGFR-2 is encoded by the gene having an Ensembl identification number ENSCAFG00000002079.

VEGFR-3 is also referred to as Flt-4, Fins Related Tyrosine Kinase 4, Vascular Endothelial Growth Factor Receptor 3, Tyrosine-Protein Kinase Receptor FLT4, Fms-Like Tyrosine Kinase 4, EC 2.7.10.1, VEGFR3, Fms-Related Tyrosine Kinase 4, EC 2.7.10, LMPH1A, LMPHM1, FLT41 or PCL. *Canis lupus familiaris* (canine) VEGFR-3 is encoded by the gene having an Ensembl identification number ENSCAFG00000000482.

RAF, as used herein, includes Raf family members: ARAF, BRAF, mutant BRAF V600E, and CRAF.

ARAF is also referred to as A-Raf Proto-Oncogene, Serine/Threonine Kinase, V-Raf Murine Sarcoma 3611 Viral Oncogene Homolog 1, Serine/Threonine-Protein Kinase A-Raf, Proto-Oncogene A-Raf-1, Proto-Oncogene Pks, EC 2.7.11.1, ARAF1, PKS2, V-Raf Murine Sarcoma 3611 Viral Oncogene-Like Protein A-Raf Proto-Oncogene Serine/Threonine-Protein Kinase. Ras-Binding Protein DA-Raf, Proto-Oncogene A-Raf, Oncogene ARAF1, EC 2.7.11, A-RAF, RAFA1, or PKS. Canis lupus familiaris (canine) ARAF is encoded by the gene having an Ensembl identification number ENSCAFG00000015115.

BRAF is also referred to as B-Raf Proto-Oncogene, Serine/Threonine Kinase, V-Raf Murine Sarcoma Viral Oncogene Homolog B1, V-Raf Murine Sarcoma Viral Oncogene Homolog B, Serine/Threonine-Protein Kinase B-Raf, Proto-Oncogene B-Raf, BRAF1, RAFB1 B-Raf Serine/Threonine-Protein, 94 KDa B-Raf Protein, EC 2.7.11.1, B-RAF1, B-Raf, NS7, or P94. Canis lupus familiaris (canine) B-RAF is encoded by the gene having an Ensembl identification number ENSCAFG00000003907.

CRAF is also referred to as Raf-1, Raf-1 Proto-Oncogene, Serine/Threonine Kinase, RAF Proto-Oncogene Serine/Threonine-Protein Kinase, V-Raf-1 Murine Leukemia Viral Oncogene Homolog 1, C-Raf Proto-Oncogene, Serine/Threonine Kinase, Proto-Oncogene C-RAF, EC 2.7.11.1, Raf-1, V-Raf-1 Murine Leukemia Viral Oncogene-Like Protein 1, Raf Proto-Oncogene Serine/Threonine Protein Kinase Oncogene RAF1, EC 2.7.11, CMD1NN, C-Raf, CRAF. CRaf, NS5, or RAF. Canis lupus familiaris (canine) CRAF is encoded by the gene having an Ensembl identification number ENSCAFG00000004951.

FLT-3 is also referred to as Fins Related Tyrosine Kinase 3, Receptor-Type Tyrosine-Protein Kinase FLT3, Stem Cell Tyrosine Kinase 1, Fms-Like Tyrosine Kinase 3, FL Cytokine Receptor, CD135 Antigen, EC 2.7.10.1, CD135, FLK-2, FLK2, STK1, Growth Factor Receptor Tyrosine Kinase Type III, Fms-Related Tyrosine Kinase 3, Fetal Liver Kinase 2, Fetal Liver Kinase-2, EC 2.7.10, FLT-3, or STK-1. Canis lupus familiaris (canine) FLT-3 is encoded by the gene having an Ensembl identification number of: ENSCAFG00000006716.

RET is also referred to as Ret Proto-Oncogene, Proto-Oncogene Tyrosine-Protein Kinase Receptor Ret, Cadherin-Related Family Member 16, Rearranged During Transfection, RET Receptor Tyrosine Kinase Cadherin Family Member 12, Proto-Oncogene C-Ret, EC 2.7.10.1, CDHF12, CDHR16, PTC, Ret Proto-Oncogene (Multiple Endocrine Neoplasia And Medullary Thyroid Carcinoma 1, Hirschsprung Disease), Multiple Endocrine Neoplasia And Medullary Thyroid Carcinoma 1, Hirschsprung Disease 1, EC 2.7.10, RET-ELE1, HSCR1, MEN2A, MEN2B, RET51, or MTC1. Canis lupus familiaris (canine) RET is encoded by the gene having an Ensembl identification number of ENSCAFG00000007076.

PDGFRB is also referred to as Platelet Derived Growth Factor Receptor, Beta Platelet-Derived Growth Factor Receptor, Beta Polypeptide, Beta-Type Platelet-Derived Growth Factor Receptor, Platelet-Derived Growth Factor Receptor Beta, Platelet-Derived Growth Factor Receptor 1, CD140 Antigen-Like Family Member B, PDGF-R-Beta, EC 2.7.10.1, PDGFR-Beta, PDGFR-1, PDGFR1, PDGFR, Beta Platelet-Derived Growth Factor Receptor, Activated Tyrosine Kinase PDGFRB•CD140b Antigen, NDEL1-PDGFRB, EC 2.7.10, CD140B, IBGC4, JTK12, PENTT, IMF1, and KOGS. Canis lupus familiaris (canine) PDGFRB is encoded by the gene having an Ensembl identification number of ENSCAFG00000018214.

It must be noted that, as used in the specification and the appended claims, the singular forms "a," "an" and "the" include plural referents unless the context clearly dictates otherwise.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b", or "a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Methods

Described herein are methods of treating canine cancers comprising administration of a therapeutically effective amount of a pharmaceutical composition comprising HDAC inhibitors, Rapamycin, Dasatinib, Lapatinib, Trametinib, Vorinostat, Imatinib, Crizotinib, Sorafenib, and combinations thereof.

Types of Cancers

Canine cancers include, but are not limited to, solid tumors, leukemia, lymphocytic leukemia, lymphoma, sarcoma, soft tissue sarcoma, multiple myeloma, hemangiosarcoma, histiocytic sarcoma, hepatocellular carcinoma, lymphosarcoma, osteosarcoma, transitional cell carcinoma, squamous cell carcinoma, subungual squamous cell carcinoma, mammary carcinoma, melanoma, mast cell tumors, lipoma, apocrine gland anal sac adenocarcinomas (AGASACA), lung cancer, pulmonary adenocarcinoma, pancreatic cancer, stomach cancer, prostate cancer, nasal cancer, liver cancer, brain cancer, bladder cancer and thyroid cancer. The methods and compositions described herein, also can be used on any other cancers, including cancers that are rare in canines.

Modes of Administration

In certain embodiments, the pharmaceutical compositions comprising the compounds described herein are administered to a subject in need thereof by oral administration. The pharmaceutical compositions can be formulated for administration to subjects by a variety of routes, including orally, intranasally, by inhalation, intramuscularly, intraperitoneally, and parenterally, including intravenously or subcutaneously. Pharmaceutical compositions can be formulated in volumes and concentrations suitable for bolus administration, for continuous infusion, or for subcutaneous administration. Pharmaceutical compositions comprising anti-cancer agents may be administered by any preferred route of administration.

Dosing Regimens

The compounds described herein can be administered in at any suitable dose. An individual dose of the compound can be any ranging from 0.01-200 mg/kg, inclusive. An individual dose of the compound can a be 1.0-100 mg/kg, 100-200 mg/kg, 1.0-10 mg/kg, 10-20 mg/kg, 20-30 mg/kg, 30-40 mg/kg, 40-50 mg/kg; 50-60 mg/kg, 70-80 mg/kg, 80-90 mg/kg, 90-100 mg/kg, 10-100 mg/kg, 100-150 mg/kg, 150-200 mg/kg, 20-50 mg/kg, 50-100 mg/kg, 1.0-20 mg/kg, 1.0-10 mg/kg, 1.0-5.0 mg/kg, 1.0-2.0 mg/kg, 5-10 mg/kg, 10-15 mg/kg, 15-20 mg/kg, 0.5-1.5 mg/kg, 0.5-1.0 mg/kg, 0.1-1.0 mg/kg, 0.1-0.2 mg/kg, 0.2-0.3 mg/kg, 0.3-0.4 mg/kg, 0.4-0.5 mg/kg, 0.5-0.6 mg/kg, 0.6-0.7 mg/kg, 0.7-0.8 mg/kg, 0.8-0.9 mg/kg, 0.9-1.0 mg/kg, 0.01-0.1 mg/kg, 0.01-0.02 mg/kg, 0.02-0.03 mg/kg, 0.03-0.04 mg/kg, 0.04-0.05 mg/kg, 0.05-0.06 mg/kg, 0.06-0.07 mg/kg, 0.07-0.08 mg/kg, 0.08-0.09 mg/kg, 0.09-0.1 mg/kg, 1.0-3.0 mg/kg, 1.1-1.2 mg/kg, 1.2-1.3 mg/kg, 1.3-1.4 mg/kg, 1.4-1.5 mg/kg, 1.5-1.6 mg/kg, 1.6-1.7 mg/kg, 1.7-1.8 mg/kg, 1.8-1.9 mg/kg, 1.9-2.0 mg/kg, 2.0-2.1 mg/kg, 2.1-2.2 mg/kg, 2.2-2.3 mg/kg, 2.3-2.4 mg/kg, 2.4-2.5 mg/kg, 2.5-2.6 mg/kg, 2.6-2.7 mg/kg, 2.7-2.8 mg/kg, 2.8-2.9 mg/kg, or 2.9-3.0 mg/kg, inclusive.

In a variety of embodiments, the pharmaceutical compositions described herein are administered for a period of 1 day to indefinitely, a period of 1 week to 6 months, a period of 3 months to 5 years, a period of 6 months to 1 or 2 years, or the like. Optionally, administration is repeated; for example, in certain embodiments, the pharmaceutical compositions described herein are administered once daily, twice daily, three times daily, four times daily, five times daily, every two days, every three days, every five days, once a week, once every two weeks, once a month, every other month, semi-annually, or annually. In certain embodiments, the pharmaceutical compositions described herein are administered at regular intervals over a period of several weeks, followed by a period of rest, during which no pharmaceutical composition described herein is administered. For example, in certain embodiments, pharmaceutical compositions comprising a compound described herein are administered for one, two, three, or more weeks, followed by one, two, three, or more weeks without pharmaceutical composition administration. The repeated administration can be at the repeated; for example, in certain embodiments, the pharmaceutical composition comprising a compound described herein is administered once daily, twice daily, three times daily, four times daily, five times daily, every two days, every three days, every five days, once a week, once every two weeks, once a month, every other month, semi-annually, or annually. In certain embodiments, the pharmaceutical composition comprising a compound is administered at regular intervals over a period of several weeks, followed by a period of rest, during which no the pharmaceutical composition comprising a compound is administered. For example, in certain embodiments, the pharmaceutical composition is administered for one, two, three, or more weeks, followed by one, two, three, or more weeks without administration of the pharmaceutical composition comprising the compound. The repeated administration can be at the same dose of a different dose.

In certain embodiments, Rapamycin is administered at a dose of 0.05-0.5 mg/kg/day. In certain embodiments, Rapamycin is administered at a dose of 0.1 mg/kg/day. In certain embodiments, Trametinib is administered at a dose of 0.01-0.1 mg/kg/day. In certain embodiments, Trametinib is administered at a dose of 0.02 mg/kg/day. In certain embodiments, Trametinib is administered at a dose of 0.01-0.05 mg/kg/day. In certain embodiments, Trametinib is administered at a dose of 0.02-0.03 mg/kg/day. In certain embodiments, Trametinib is administered at a dose of 0.02 mg/kg/day. In certain embodiments, Trametinib is administered at a dose of 0.03 mg/kg/day. In certain embodiments, Lapatinib is administered at a dose of 1-20 mg/kg/day. In certain embodiments, Lapatinib is administered at a dose of 5-10 mg/kg/day. In certain embodiments, Lapatinib is administered at a dose of 5 mg/kg/day. In certain embodiments, Lapatinib is administered at a dose of 6 mg/kg/day. In certain embodiments, Lapatinib is administered at a dose of 7 mg/kg/day. In certain embodiments, Lapatinib is administered at a dose of 8 mg/kg/day. In certain embodiments, Lapatinib is administered at a dose of 9 mg/kg/day. In certain embodiments, Lapatinib is administered at a dose of 10 mg/kg/day. In certain embodiments, Dasatinib is administered at a dose of 0.1-1.0 mg/kg/day. In certain embodiments, Dasatinib is administered at a dose of 0.5-0.7 mg/kg/day. In certain embodiments, Dasatinib is administered at a dose of 0.5 mg/kg/day. In certain embodiments, Dasatinib is administered at a dose of 0.6 mg/kg/day. In certain embodiments, Dasatinib is administered at a dose of 0.7 mg/kg/day. In certain embodiments, Vorinostat is administered at a dose 10-100 mg/kg/every other day. In certain embodiments, Vorinostat is administered at a dose 30-60 mg/kg/every other day. In certain embodiments, Vorinostat is administered at a dose 45 mg/kg/every other day. In certain embodiments, Imatinib is administered at a dose 1-100 mg/kg/day. In certain embodiments, Imatinib is administered at a dose of 10 mg/kg/day. In certain embodiments, Crizotinib is administered at a dose of 0.5-5.0 mg/kg/day. In certain embodiments, Crizotinib is administered at a dose of 1 mg/kg/day-2 mg/kg/day. In certain embodiments, Crizotinib is administered at a dose of 1 mg/kg/day. In certain embodiments, Sorafinib is administered at a dose of 0.5-5.0 mg/kg/day. In certain embodiments, Sorafinib is administered at a dose of 1 mg/kg/day-3 mg/kg/day. In certain embodiments, Sorafinib is administered at a dose of 1 mg/kg/day. In certain embodiments, Sorafinib is administered at a dose of 2 mg/kg/day. In certain embodiments, Sorafinib is administered at a dose of 3 mg/kg/day. In certain embodiments, Sorafinib is administered at a dose of 3 mg/kg/every other day. In certain embodiments, Sorafinib is administered at a dose of 3 mg/kg/week.

In certain embodiments, the subject has transitional cell carcinoma, and the subject is treated with Lapatinib. In certain embodiments, the subject has transitional cell carcinoma and the subject is treated with Lapatinib at a dose of 5-10 mg/kg/day. In certain embodiments, the subject has transitional cell carcinoma, and the subject is treated with Trametinib. In certain embodiments, the subject has transitional cell carcinoma, and the subject is treated with Trametinib at a dose of 0.02-0.03 mg/kg/day.

In certain embodiments, the subject has thyroid cancer, and the subject is treated with Lapatinib. In certain embodiments, the subject has thyroid cancer, and the subject is treated with Lapatinib at a dose of 5-10 mg/kg/day. In certain embodiments, the subject has thyroid cancer, and the subject is treated with Trametinib. In certain embodiments, the subject has thyroid cancer, and the subject is treated with Trametinib at a dose of 0.02-0.03 mg/kg/day. In certain embodiments, the subject has thyroid cancer, and the subject is treated with Rapamycin. In certain embodiments, the subject has thyroid cancer, and the subject is treated with Rapamycin at a dose of 0.05-2 mg/kg/day. In certain embodiments, the subject has thyroid cancer, and the subject is treated with Rapamycin at a dose of 0.1 mg/kg/day.

In certain embodiments, the subject has squamous cell carcinoma, and the subject is treated with Lapatinib. In certain embodiments, the subject has squamous cell carcinoma, and the subject is treated with Lapatinib at a dose of 5-10 mg/kg/day. In certain embodiments, the subject has squamous cell carcinoma, and the subject is treated with Trametinib. In certain embodiments, the subject has squamous cell carcinoma, and the subject is treated with Trametinib at a dose of 0.02-0.03 mg/kg/day.

In certain embodiments, the subject has soft tissue sarcoma, and the subject is treated with Trametinib. In certain embodiments, the subject has soft tissue sarcoma, and the subject is treated with Trametinib at a dose of 0.02-0.03 mg/kg/day. In certain embodiments, the subject has soft tissue sarcoma, and the subject is treated with Rapamycin. In certain embodiments, the subject has soft tissue sarcoma, and the subject is treated with Rapamycin at a dose of 0.05-2 mg/kg/day. In certain embodiments, the subject has soft tissue sarcoma, and the subject is treated with Rapamycin at a dose of 0.1 mg/kg/day. In certain embodiments, the subject has soft tissue sarcoma, and the subject is treated with Dasatinib. In certain embodiments, the subject has soft tissue sarcoma, and the subject is treated with Dasatinib at a dose of 0.1-1.0 mg/kg/day. In certain embodiments, the subject has soft tissue sarcoma, and the subject is treated with Dasatinib at a dose of 0.5-0.7 mg/kg/day.

In certain embodiments, the subject has pulmonary adenocarcinoma, and the subject is treated with Lapatinib. In certain embodiments, the subject has pulmonary adenocarcinoma and the subject is treated with Lapatinib at a dose of 5-10 mg/kg/day. In certain embodiments, the subject has pulmonary adenocarcinoma, and the subject is treated with Trametinib. In certain embodiments, the subject has pulmonary adenocarcinoma, and the subject is treated with Trametinib at a dose of 0.02-0.03 mg/kg/day.

In certain embodiments, the subject has osteosarcoma, and the subject is treated with Rapamycin. In certain embodiments, the subject has osteosarcoma, and the subject is treated with Rapamycin at a dose of 0.05-2 mg/kg/day. In certain embodiments, the subject has osteosarcoma, and the subject is treated with Rapamycin at a dose of 0.1 mg/kg/day. In certain embodiments, the subject has osteosarcoma, and the subject is treated with Dasatinib. In certain embodiments, the subject has osteosarcoma, and the subject is treated with Dasatinib at a dose of 0.1-1.0 mg/kg/day. In certain embodiments, the subject has osteosarcoma, and the subject is treated with Dasatinib at a dose of 0.5-0.7 mg/kg/day.

In certain embodiments, the subject has melanoma, and the subject is treated with Rapamycin. In certain embodiments, the subject has melanoma, and the subject is treated with Rapamycin at a dose of 0.05-2 mg/kg/day. In certain embodiments, the subject has melanoma, and the subject is treated with Rapamycin at a dose of 0.1 mg/kg/day. In certain embodiments, the subject has melanoma, and the subject is treated with Dasatinib. In certain embodiments, the subject has melanoma, and the subject is treated with Dasatinib at a dose of 0.1-1.0 mg/kg/day. In certain embodiments, the subject has melanoma, and the subject is treated with Dasatinib at a dose of 0.5-0.7 mg/kg/day. In certain embodiments, the subject has melanoma, and the subject is treated with Trametinib. In certain embodiments, the subject has melanoma, and the subject is treated with Trametinib at a dose of 0.02-0.03 mg/kg/day.

In certain embodiments, the subject has mast cell tumor(s), and the subject is treated with Imatinib. In certain embodiments, the subject has mast cell tumor(s), and the subject is treated with Imatinib at a dose of 1-20 mg/kg/day. In certain embodiments, the subject has mast cell tumor(s), and the subject is treated with Imatinib at a dose of 10 mg/kg/day.

In certain embodiments, the subject has histocytic sarcoma, and the subject is treated with Trametinib. In certain embodiments, the subject has histocytic sarcoma, and the subject is treated with Trametinib at a dose of 0.02-0.03 mg/kg/day. In certain embodiments, the subject has histocytic sarcoma, and the subject is treated with Vorinostat. In certain embodiments, the subject has histocytic sarcoma, and the subject is treated with Vorinostat at a dose of 10-50 mg/kg/day. In certain embodiments, the subject has histocytic sarcoma, and the subject is treated with Vorinostat at a dose of 30 mg/kg/day.

In certain embodiments, the subject has hepatocellular carcinoma, and the subject is treated with Vorinostat. In certain embodiments, the subject has hepatocellular carcinoma, and the subject is treated with Vorinostat at a dose of 10-50 mg/kg/day. In certain embodiments, the subject has hepatocellular carcinoma, and the subject is treated with Vorinostat at a dose of 30 mg/kg/day. In certain embodiments, the subject has hepatocellular carcinoma, and the subject is treated with Rapamycin. In certain embodiments, the subject has hepatocellular carcinoma, and the subject is treated with Rapamycin at a dose of 0.05-2 mg/kg/day. In certain embodiments, the subject has hepatocellular carcinoma, and the subject is treated with Rapamycin at a dose of 0.1 mg/kg/day.

In certain embodiments, the subject has hemangiosarcoma, and the subject is treated with Rapamycin. In certain embodiments, the subject has hemangiosarcoma, and the subject is treated with Rapamycin at a dose of 0.05-2 mg/kg/day. In certain embodiments, the subject has hemangiosarcoma, and the subject is treated with Rapamycin at a dose of 0.1 mg/kg/day. In certain embodiments, the subject has hemangiosarcoma, and the subject is treated with Vorinostat. In certain embodiments, the subject has hemangiosarcoma, and the subject is treated with Vorinostat at a dose of 10-50 mg/kg/day. In certain embodiments, the subject has hemangiosarcoma, and the subject is treated with Vorinostat at a dose of 30 mg/kg/day. In certain embodiments, the subject has hemangiosarcoma, and the subject is treated with Dasatinib. In certain embodiments, the subject has hemangiosarcoma, and the subject is treated with Dasatinib at a dose of 0.1-1.0 mg/kg/day. In certain embodiments, the subject has hemangiosarcoma, and the subject is treated with Dasatinib at a dose of 0.5-0.7 mg/kg/day. In certain embodiments, the subject has hemangiosarcoma, and the subject is treated with Trametinib. In certain embodiments, the subject has hemangiosarcoma, and the subject is treated with Trametinib at a dose of 0.02-0.03 mg/kg/day.

In certain embodiments, the subject has apocrine gland anal sac adenocarcinoma (AGASACA), and the subject is treated with Trametinib. In certain embodiments, the subject has AGASACA, and the subject is treated with Trametinib at a dose of 0.02-0.03 mg/kg/day. In certain embodiments, the subject has AGASACA, and the subject is treated with Lapatinib. In certain embodiments, the subject has AGASACA and the subject is treated with Lapatinib at a dose of 5-10 mg/kg/day.

Diagnostic Assays

In certain embodiments, described herein are methods of identifying subjects with cancer that will respond to pharmaceutical compositions comprising a compound described herein. In various embodiments, described herein are methods of treating cancer in a canine subject comprising administration of pharmaceutical compositions comprising a compound described herein and further comprising the step of determining or having determined if the cancer harbors at least one mutation in one or more genes prior to the administration of the pharmaceutical composition comprising a compound described herein. In various embodiments, described herein are methods of treating cancer in a canine subject comprising administration of pharmaceutical compositions comprising a compound described herein and further comprising the step of determining or having determined if the cancer overexpresses or underexpresses one or more genes compared to non-cancerous tissue prior to the administration of the pharmaceutical composition comprising a compound described herein. In certain embodiments, at least one mutation in at least one gene is ATM kinase, prior to the administration of a pharmaceutical composition comprising a HDAC inhibitor. In certain embodiments, at least one mutation in at least one gene is selected from the group consisting of mTOR, PI3K, AKT and Ras, prior to the administration of a pharmaceutical composition comprising Rapamycin. In certain embodiments, at least one mutation in at least one gene is a gene that regulates or is regulated by mTOR, PI3K, AKT and Ras. In certain embodiments, at least one mutation in at least one gene is selected from the group consisting of ABL, BCR-ABL, c-KIT, EPHA2, PDGFR and a Src Family Kinase prior to the administration of a pharmaceutical composition comprising Dasatinib. In certain embodiments, at least one mutation in at least one gene is selected from the group consisting of ERBB1 and ERBB2 prior to the administration a pharmaceutical composition comprising Lapatinib. In certain embodiments, at least one mutation in at least one gene is selected from the group consisting of MEK1 and MEK2 prior to the administration of a pharmaceutical composition comprising Trametinib. In certain embodiments, at least one mutation in at least one gene is selected from the group consisting of p300, CBP, TIF-2, RAR, BCL-6, AML1, STAT5 and HDAC1 prior to the administration of a pharmaceutical composition comprising Vorinostat. In certain embodiments, at least one mutation in at least one gene is selected from the group consisting of ABL, BCR-ABL, PDGFR, and C-KIT prior to the administration of a pharmaceutical composition comprising Imatinib. In certain embodiments, at least one mutation in at least one gene is a gene that regulates or is regulated by of ALK, c-MET and ROS1 prior to the administration of a pharmaceutical composition comprising Crizotinib. In certain embodiments, at least one mutation in at least one gene is selected from the group consisting of RAF, c-Kit, FLT-3, RET, VEGFRs and PDGFRB prior to the administration of a pharmaceutical composition comprising Sorafenib. In certain embodiments, the determining at least one mutation in at least one gene is determined from a biological sample derived from the cancer. In certain embodiments, the biological sample comprises nucleic acid. The nucleic acid can be DNA, RNA or combinations thereof. Any method known in the art can be used to determine the sequence of a gene. In certain embodiments, the determining is performed by sequencing nucleic acid.

In certain aspects, the mutation is a splice variant, a frameshift, a missense, or a nonsense mutation. In certain aspects, the at least one mutation of at least one gene is shown in Tables 1, 2 or 12-26. In certain aspects, the at least one mutation is a mutation in the ATM gene is shown in Table 2. In certain embodiments, the cancer harbors a mutation in one or more genes selected from a gene listed in Tables 1, 2 and 12-26. In certain embodiments, the cancer harbors a mutation in one or more genes selected from a gene listed in Tables 1, 2 and 12-26, the cancer is one listed in Tables 1, 2 and 12-26 and the cancer is treated with a targeted drug listed in Tables 1, 2 and 12-26.

In certain aspects, the at least one mutation is a mutation in BRAF. In certain aspects, the at least one mutation is a mutation in SETD2. In certain aspects, the at least one mutation is a mutation in PDGFRβ. In certain aspects, the at least one mutation is a mutation in Notch 1. In certain aspects, the at least one mutation is a mutation in p53. In certain aspects, the at least one mutation is a mutation in PIK3CA. In certain aspects, the at least one mutation is a mutation in PTEN.

In certain embodiments, the biological sample is derived from a subject with transitional cell carcinoma, it is determined that the cancer harbors a mutation in BRAF, and the subject is selected for treatment with Lapatinib, Trametinib or combinations thereof. In certain embodiments, the biological sample is derived from a subject with thyroid cancer, the cancer harbors a mutation in Notch1, and the subject is selected for treatment with Trametinib, Lapatinib, Rapamycin, or combinations thereof. In certain embodiments, the biological sample is derived from a subject with squamous cell carcinoma, it is determined that the cancer harbors a mutation in PDGFRβ, and the subject is selected for treatment with Trametinib, Lapatinib, or combinations thereof. In certain embodiments, the biological sample is derived from a subject with squamous cell carcinoma, it is determined that the cancer harbors a mutation in SETD2, and the subject is selected for treatment with Trametinib, Lapatinib, or combinations thereof. In certain embodiments, the biological sample is derived from a subject with soft tissue sarcoma, it is determined that the cancer harbors a mutation in SETD2, and the subject is selected for treatment with trametinib, dasatinib, rapamycin, or combinations thereof. In certain embodiments, the biological sample is derived from a subject with soft tissue sarcoma, it is determined that the cancer harbors a mutation in ATM, and the subject is selected for treatment with trametinib, dasatinib, rapamycin, or combinations thereof. In certain embodiments, the biological sample is derived from a subject with has osteosarcoma, it is determined that the cancer harbors a mutation in SETD2, and the subject is selected for treatment with dasatinib, rapamycin, or combinations thereof. In certain embodiments, the biological sample is derived from a subject with melanoma, it is determined that the cancer harbors a mutation in SETD2, and the subject is selected for treatment with trametinib, dasatinib, rapamycin, or combinations thereof. In certain embodiments, the biological sample is derived from a subject with mast cell tumor, it is determined that the cancer harbors a mutation in SETD2, and the subject is selected for treatment with imatinib. In certain embodiments, the biological sample is derived from a subject with mast cell tumor, it is determined that the cancer harbors a mutation in PDGFRβ, and the subject is selected for treatment with imatinib. In certain embodiments, the biological sample is derived from a subject with mast cell tumor, it is determined that the cancer harbors a mutation in Notch1, and the subject is selected for treatment with imatinib. In certain embodiments, the biological sample is derived from a subject with hemangiosarcoma sarcoma, it is determined that the cancer harbors a mutation in PIK3CA, and the subject is selected for treatment with Rapamycin, Trametinib, Dasatinib, Vorinostat, or combinations thereof. In certain embodiments, the biological sample is derived from a subject with hemangiosarcoma sarcoma, it is determined that the cancer harbors a mutation in p53, and the subject is selected for treatment with Rapamycin, Trametinib, Dasatinib, Vorinostat, or combinations thereof. In certain embodiments, the biological sample is derived from a subject with hemangiosarcoma sarcoma, it is determined that the cancer harbors a mutation in PTEN, and the subject is selected for treatment with Rapamycin, Trametinib, Dasatinib, Vorinostat, or combinations thereof. In certain embodiments, the biological sample is derived from a subject with hemangiosarcoma, it is determined that the cancer harbors a mutation in Notch1, and the subject is selected for treatment with Rapamycin, Trametinib, Dasatinib, Vorinostat, or combinations thereof.

In certain embodiments, the subject has transitional cell carcinoma, the cancer harbors a mutation in BRAF and the subject is treated with Lapatinib, Trametinib or combinations thereof. In certain embodiments, the subject has thyroid cancer, the cancer harbors a mutation in Notch1, and the subject is treated with Trametinib, Lapatinib, Rapamycin, or combinations thereof. In certain embodiments, the subject has squamous cell carcinoma, the cancer harbors a mutation in PDGFRβ, and the subject is treated with Trametinib, Lapatinib, or combinations thereof. In certain embodiments, the subject has squamous cell carcinoma, the cancer harbors a mutation in SETD2, and the subject is treated with Trametinib, Lapatinib, or combinations thereof. In certain embodiments, the subject has soft tissue sarcoma, the cancer harbors a mutation in SETD2, and the subject is treated with trametinib, dasatinib, rapamycin, or combinations thereof. In certain embodiments, the subject has soft tissue sarcoma, the cancer harbors a mutation in ATM, and the subject is treated with trametinib, dasatinib, rapamycin, or combinations thereof. In certain embodiments, the subject has osteosarcoma, the cancer harbors a mutation in SETD2, and the subject is treated with dasatinib, rapamycin, or combinations thereof. In certain embodiments, the subject has melanoma, the cancer harbors a mutation in SETD2, and the subject is treated with trametinib, dasatinib, rapamycin, or combinations thereof. In certain embodiments, the subject has mast cell tumor, the cancer harbors a mutation in SETD2, and the subject is treated with imatinib. In certain embodiments, the subject has mast cell tumor, the cancer harbors a mutation in PDGFRβ, and the subject is treated with imatinib. In certain embodiments, the subject has mast cell tumor, the cancer harbors a mutation in Notch1, and the subject is treated with imatinib. In certain embodiments, the subject has hemangiosarcoma sarcoma, the cancer harbor a mutation in PIK3CA, and the subject is treated with Rapamycin, Trametinib, Dasatinib, Vorinostat, or combinations thereof. In certain embodiments, the subject has hemangiosarcoma sarcoma, the cancer harbor a mutation in p53, and the subject is treated with Rapamycin, Trametinib, Dasatinib, Vorinostat, or combinations thereof. In certain embodiments, the subject has hemangiosarcoma sarcoma, the cancer harbor a mutation in PTEN, and the subject is treated with Rapamycin, Trametinib, Dasatinib, Vorinostat, or combinations thereof. In certain embodiments, the subject has hemangiosarcoma sarcoma, the cancer harbor a mutation in Notch1, and the subject is treated with Rapamycin, Trametinib, Dasatinib, Vorinostat, or combinations thereof.

In certain embodiments, the determining if the cancer overexpresses or underexpresses one or more genes compared to non-cancerous tissue prior to the administration of the pharmaceutical composition is determined from a biological sample derived from the cancer. In certain embodiments, the biological sample comprises nucleic acid. The nucleic acid can be DNA, RNA or combinations thereof. Any method known in the art can be used to determine the expression of a gene, such as, but not limited to, immunohistochemistry, quantitative PCR and RNA-Seq. In certain embodiments, the one or more genes overexpressed or underexpressed in the cancer is a gene listed in Tables 1, and 12-26. In certain embodiments, the cancer overexpresses or underexpresses one or more genes compared to non-cancerous tissue selected from a gene listed in Tables 1, and 12-26. In certain embodiments, the cancer overexpresses or underexpresses one or more genes compared to non-cancerous tissue selected from a gene listed in Tables 1, and 12-26, the cancer is one listed in Tables 1, and 12-26, and the cancer is treated with a targeted drug listed in Tables 1 and 12-26.

In certain embodiments, the cancer is Transitional Cell Carcinoma and the gene that is overexpressed is ERBB2. In certain embodiments, the cancer is Transitional Cell Carcinoma, the gene that is overexpressed is ERBB2, and the cancer harbors a mutation in BRAF. In certain embodiments, the cancer is Transitional Cell Carcinoma, the gene that is overexpressed is ERBB2, and the subject is treated with Lapatinib, Trametinib, or combinations thereof. In certain embodiments, the cancer is Transitional Cell Carcinoma, the gene that is overexpressed is ERBB2, the cancer harbors a mutation in BRAF, and the subject is treated with Lapatinib, Trametinib, or combinations thereof.

In certain embodiments, the cancer is Thyroid Carcinoma and the gene that is overexpressed is one or more genes shown in Table 13. In certain embodiments, the cancer is Thyroid Carcinoma, the gene that is overexpressed is one or more genes shown in Table 13, and the cancer harbors a mutation in one or more genes shown in Table 13. In certain embodiments, the cancer is Thyroid Carcinoma, the gene that is overexpressed is one or more genes shown in Table 13, the cancer harbors a mutation in one or more genes shown in Table 13, and the subject is treated with Lapatinib, Trametinib, Rapamycin or combinations thereof.

In certain embodiments, the cancer is Squamous Cell Carcinoma and the gene that is overexpressed is one or more genes shown in Table 15. In certain embodiments, the cancer is Squamous Cell Carcinoma, the gene that is overexpressed is one or more genes shown in Table 15, and the cancer harbors a mutation in one or more genes shown in Table 15. In certain embodiments, the cancer is Squamous Cell Carcinoma, the gene that is overexpressed is one or more genes shown in Table 15, the cancer harbors a mutation in one or more genes shown in Table 15, and the subject is treated with Lapatinib, Trametinib, or combinations thereof. In certain embodiments, the cancer is Squamous Cell Carcinoma, the gene that is overexpressed is PDGFRβ or SETD2, the cancer harbors a mutation in PDGFRβ or SETD2, and the subject is treated with Lapatinib, Trametinib, or combinations thereof.

In certain embodiments, the cancer is Soft Tissue Sarcoma, and the gene that is overexpressed is one or more genes shown in Table 16. In certain embodiments, the cancer is Soft Tissue Sarcoma, the gene that is overexpressed is one or more genes shown in Table 16, and the cancer harbors a mutation in one or more genes shown in Table 16. In certain embodiments, the cancer is Soft Tissue Sarcoma, the gene that is overexpressed is one or more genes shown in Table 16, the cancer harbors a mutation in one or more genes shown in Table 16, and the subject is treated with Rapamycin, Dasatinib, Trametinib, or combinations thereof. In certain embodiments, the cancer is Soft Tissue Sarcoma, the gene that is overexpressed is one or more genes shown in Table 16, the cancer harbors a mutation in ATM or SETD2, and the subject is treated with Rapamycin, Dasatinib Trametinib, or combinations thereof.

In certain embodiments, the cancer is Pulmonary Adenocarcinoma, and the gene that is overexpressed is one or more genes shown in Table 17. In certain embodiments, the cancer is Pulmonary Adenocarcinoma, the gene that is overexpressed is one or more genes shown in Table 17, and the cancer harbors a mutation in one or more genes shown in Table 17. In certain embodiments, the cancer is Pulmonary Adenocarcinoma, the gene that is overexpressed is one or more genes shown in Table 17, the cancer harbors a mutation in one or more genes shown in Table 17, and the subject is treated with Lapatinib, Trametinib, or combinations thereof. In certain embodiments, the cancer is Pulmonary Adenocarcinoma, the gene that is overexpressed is one or more genes shown in Table 17, the cancer harbors a mutation in Table 17, and the subject is treated with Lapatinib, Trametinib, or combinations thereof.

In certain embodiments, the cancer is Osteosarcoma, and the gene that is overexpressed is one or more genes shown in Table 18. In certain embodiments, the cancer is Osteosarcoma, the gene that is overexpressed is one or more genes shown in Table 18, and the cancer harbors a mutation in one or more genes shown in Table 18. In certain embodiments, the cancer is Osteosarcoma, the gene that is overexpressed is one or more genes shown in Table 18, and the cancer harbors a mutation in SETD2. In certain embodiments, the cancer is Osteosarcoma, the gene that is overexpressed is one or more genes shown in Table 18, the cancer harbors a mutation in one or more genes shown in Table 18, and the subject is treated with Dasatinib, Rapamycin, or combinations thereof. In certain embodiments, the cancer is Osteosarcoma, the gene that is overexpressed is one or more genes shown in Table 18, the cancer harbors a mutation in Table 18, and the subject is treated with Dasatinib, Rapamycin, or combinations thereof. In certain embodiments, the cancer is Osteosarcoma, the gene that is overexpressed is one or more genes shown in SETD2, the cancer harbors a mutation in Table 18, and the subject is treated with Dasatinib, Rapamycin, or combinations thereof.

In certain embodiments, the cancer is Melanoma, and the gene that is overexpressed is one or more genes shown in Table 19. In certain embodiments, the cancer is Melanoma, the gene that is overexpressed is one or more genes shown in Table 19, and the cancer harbors a mutation in one or more genes shown in Table 19. In certain embodiments, the cancer is Melanoma, the gene that is overexpressed is one or more genes shown in Table 19, and the cancer harbors a mutation in SETD2. In certain embodiments, the cancer is Melanoma, the gene that is overexpressed is one or more genes shown in Table 19, the cancer harbors a mutation in one or more genes shown in Table 19, and the subject is treated with Dasatinib, Rapamycin, Trametinib or combinations thereof. In certain embodiments, the cancer is Melanoma, the gene that is overexpressed is one or more genes shown in Table 19, the cancer harbors a mutation in Table 19, and the subject is treated with Dasatinib, Rapamycin, Trametinib or combinations thereof. In certain embodiments, the cancer is Melanoma, the gene that is overexpressed is one or more genes shown in SETD2, the cancer harbors a mutation in Table 19, and the subject is treated with Dasatinib, Rapamycin, Trametinib or combinations thereof.

In certain embodiments, the cancer is Mast Cell Tumor, and the gene that is overexpressed is one or more genes shown in Table 20. In certain embodiments, the cancer is Mast Cell Tumor, the gene that is overexpressed is one or more genes shown in Table 20, and the cancer harbors a mutation in one or more genes shown in Table 20. In certain embodiments, the cancer is Mast Cell Tumor, the gene that is overexpressed is one or more genes shown in Table 20, and the cancer harbors a mutation in SETD2, PDGFRβ, Notch1, or combinations thereof. In certain embodiments, the cancer is Mast Cell Tumor, the gene that is overexpressed is one or more genes shown in Table 20, the cancer harbors a mutation in one or more genes shown in Table 20, and the subject is treated with Imatinib. In certain embodiments, the cancer is Mast Cell Tumor, the gene that is overexpressed is SETD2, PDGFRβ, Notch1, or combinations thereof, the cancer harbors a mutation in SETD2, PDGFRβ, Notch1, or combinations thereof, and the subject is treated with Imatinib. In certain embodiments, the cancer is Mast Cell Tumor, the gene that is overexpressed is one or more genes shown in Table 18, the cancer harbors a mutation in Table 20, and the subject is treated with Imatinib. In certain embodiments, the cancer is Mast Cell Tumor, the gene that is overexpressed is one or more genes shown in SETD2, PDGFRβ, Notch1, or combinations thereof the cancer harbors a mutation in Table 20, and the subject is treated with Imatinib.

In certain embodiments, the cancer is Histiocytic Sarcoma, and the gene that is overexpressed is one or more genes shown in Table 23. In certain embodiments, the cancer is Histiocytic Sarcoma, the gene that is overexpressed is one or more genes shown in Table 23, and the cancer harbors a mutation in one or more genes shown in Table 23. In certain embodiments, the cancer is Histiocytic Sarcoma, the gene that is overexpressed is one or more genes shown in Table 23, the cancer harbors a mutation in one or more genes shown in Table 23, and the subject is treated with Vorinostat, Trametinib, or combinations thereof. In certain embodiments, the cancer is Histiocytic Sarcoma, the gene that is overexpressed is one or more genes shown in Table 23, the cancer harbors a mutation in Table 23, and the subject is treated with Vorinostat, Trametinib, or combinations thereof.

In certain embodiments, the cancer is Hepatocellular Carcinoma, and the gene that is overexpressed is one or more genes shown in Table 24. In certain embodiments, the cancer is Hepatocellular Carcinoma, the gene that is overexpressed is one or more genes shown in Table 24, and the cancer harbors a mutation in one or more genes shown in Table 24. In certain embodiments, the cancer is Hepatocellular Carcinoma, the gene that is overexpressed is one or more genes shown in Table 24, the cancer harbors a mutation in one or more genes shown in Table 24, and the subject is treated with Vorinostat, Rapamycin, or combinations thereof. In certain embodiments, the cancer is Hepatocellular Carcinoma, the gene that is overexpressed is one or more genes shown in Table 24, the cancer harbors a mutation in Table 24, and the subject is treated with Vorinostat, Rapamycin, or combinations thereof In certain embodiments, the cancer is Hemangiosarcoma, and the gene that is overexpressed is one or more genes shown in Table 25. In certain embodiments, the cancer is Hemangiosarcoma, the gene that is overexpressed is one or more genes shown in Table 25, and the cancer harbors a mutation in one or more genes shown in Table 25. In certain embodiments, the cancer is Hemangiosarcoma, the gene that is overexpressed is one or more genes shown in Table 25, and the cancer harbors a mutation in PIK3CA, p53, PTEN, NOTCH1, or combinations thereof. In certain embodiments, the cancer is Hemangiosarcoma, the gene that is overexpressed is one or more genes shown in Table 25, the cancer harbors a mutation in one or more genes shown in Table 25, and the subject is treated with Rapamycin, Trametinib, Dasatinib, Vorinostat, or combinations thereof. In certain embodiments, the cancer is Hemangiosarcoma, the gene that is overexpressed is PIK3CA, p53, PTEN, NOTCH1, or combinations thereof, the cancer harbors a mutation in PIK3CA, p53, PTEN, NOTCH1, or combinations thereof, and the subject is treated with Rapamycin, Trametinib, Dasatinib, Vorinostat, or combinations thereof. In certain embodiments, the cancer is Hemangiosarcoma, the gene that is overexpressed is one or more genes shown in Table 18, the cancer harbors a mutation in Table 25, and the subject is treated with Rapamycin, Trametinib, Dasatinib, Vorinostat, or combinations thereof. In certain embodiments, the cancer is Hemangiosarcoma, the gene that is overexpressed is one or more genes shown in PIK3CA, p53, PTEN, NOTCH1, or combinations thereof the cancer harbors a mutation in Table 25, and the subject is treated with Rapamycin, Trametinib, Dasatinib, Vorinostat, or combinations thereof.

In certain embodiments, the cancer is AGASACA, and the gene that is overexpressed is one or more genes shown in Table 26. In certain embodiments, the cancer is AGASACA, the gene that is overexpressed is one or more genes shown in Table 26, and the cancer harbors a mutation in one or more genes shown in Table 26. In certain embodiments, the cancer is AGASACA, the gene that is overexpressed is one or more genes shown in Table 26, the cancer harbors a mutation in one or more genes shown in Table 26, and the subject is treated with Lapatinib, Trametinib, or combinations thereof. In certain embodiments, the cancer is AGASACA, the gene that is overexpressed is one or more genes shown in Table 26, the cancer harbors a mutation in Table 26, and the subject is treated with Lapatinib, Trametinib, or combinations thereof.

Combination Therapies

Administration of the pharmaceutical compositions described herein comprising a compound described herein can be concurrent with (at the same time), sequential to (at a different time but on the same day, e.g., during the same subject visit), or separate from (on a different day) administration of anther anti-cancer agent or therapy. When administered sequentially or separately, the pharmaceutical compositions comprising a compound described herein can be administered before, after, or both before and after the other anti-cancer agent or therapy. In certain embodiments, the additional therapy is surgery. In certain embodiments, the additional therapy is administration of ionizing radiation to the subject.

Compounds

The structure and methods of production of Rapamycin are known in the art. For example, methods of production of Rapamycin are described in U.S. Pat. Nos. 3,929,992 and 3,993,749 which are hereby incorporated by reference in their entirety. The structure of Rapamycin is described in Findlay et al in Can. J. of Chem 58, 579 (1980). In certain embodiments, the pharmaceutical compositions described herein may also comprise derivatives of Rapamycin that are known in the art.

The structure and methods of production of Dasatinib are known in the art. For example, the structure and methods of production of Dasatinib are described in U.S. Pat. Nos. 6,596,746; 7,491,725; 7,153,856; 7,125,875; and 8,680,103; which are hereby incorporated by reference in their entirety. In certain embodiments, the pharmaceutical compositions described herein may also comprise derivatives of Dasatinib.

The structure and methods of production of Lapatinib are known in the art. For example, the structure and methods of production of Lapatinib are described in U.S. Pat. Nos. 6,713,485; 6,727,256; 7,157,466; 8,513,262; 8,821,927 which are hereby incorporated by reference in their entirety. In certain embodiments, the pharmaceutical compositions described herein may also comprise derivatives of Lapatinib that are known in the art.

The structure and methods of production of Trametinib are known in the art. For example, the structure and methods of production of Trametinib are described in U.S. Pat. Nos. 7,378,423; 8,580,304; 8,703,781; 8,835,443; 8,952,018; 9,155,706; 9,271,941. which are hereby incorporated by reference in their entirety. In certain embodiments, the pharmaceutical compositions described herein may also comprise derivatives of Trametinib that are known in the art.

The structure and methods of production of Vorinostat are known in the art. For example, the structure and methods of production of Vorinostat are described in U.S. Pat. Nos. 7,399,787; 7,456,219; 7,652,069; 7,732,490; 7,851,509; 8,067,472; 8,093,295; 8,101,663; and 8,450,372, which are hereby incorporated by reference in their entirety. In certain embodiments, the pharmaceutical compositions described herein may also comprise derivatives of Vorinostat that are known in the art.

The structure and methods of production of Imatinib are known in the art. For example, the structure and methods of production of Imatinib are described in U.S. Pat. Nos. 6,894,051 and 6,958,335 which are hereby incorporated by reference in their entirety. In certain embodiments, the pharmaceutical compositions described herein may also comprise derivatives of Imatinib that are known in the art.

The structure and methods of production of Crizotinib are known in the art. For example, the structure and methods of production of Crizotinib are described in U.S. Pat. Nos. 7,230,098, 7,825,137, 7,858,643, 8,217,057, and 8,785,632 which are hereby incorporated by reference in their entirety. In certain embodiments, the pharmaceutical compositions described herein may also comprise derivatives of Crizotinib that are known in the art.

The structure and methods of production of Sorafenib are known in the art. For example, the structure and methods of production of Sorafenib are described in U.S. Pat. Nos. 7,235,576, 7,351,834, 7,897,623, 8,124,630, 8,618,141, 8,841,330, 8,877,933, and 9,737,488 which are hereby incorporated by reference in their entirety. In certain embodiments, the pharmaceutical compositions described herein may also comprise derivatives of Sorafenib that are known in the art.

Anti-Cancer Agents

The pharmaceutical compositions described herein can be administered alone or in combination with other treatments, either simultaneously or sequentially dependent upon the condition to be treated. One or more additional anti-cancer agents may be administered to the subject. Anti-cancer agents can be, but are not limited to, chemotherapeutic agents, targeted therapies, hormones, and immunotherapies. Anti-cancer agents can be, but are not limited to, a small molecule, an antibody or antibody fragment, nucleic acid (e.g., DNA or RNA), carbohydrates, peptides, lipids, exosomes, cells, or combinations thereof. Chemotherapeutic agents include, but are not limited to alkylating agents, antimetabolites, anti-tumor antibiotics (e.g., doxorubicin, daunorubicin, bleomycin, dactinomycin), topoisomerase inhibitors (e.g., etoposide, irinotecan, topotecan), and mitotic inhibitors (e.g., docetaxel, eribulin, ixabepilone, paclitaxel, vinblastine). Examples of anti-cancer agents include, but are not limited to: Abemaciclib, Abiraterone Acetate, Abraxane (Paclitaxel Albumin-stabilized Nanoparticle Formulation), Acalabrutinib, Actemra (Tocilizumab), Adcetris (Brentuximab Vedotin), Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alpelisib, Alunbrig (Brigatinib), Ameluz (Aminolevulinic Acid Hydrochloride), Amifostine, Aminolevulinic Acid Hydrochloride, Anastrozole, Apalutamide, Aprepitant, Aranesp (Darbepoetin Alfa), Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Asparlas (Calaspargase Pegol-mknl), Atezolizumab, Avastin (Bevacizumab), Avelumab, Axicabtagene Ciloleucel, Axitinib, Azacitidine, Azedra (Iobenguane 1131), Balversa (Erdafitinib), Bavencio (Avelumab), Beleodaq (Belinostat), Belinostat, Bendamustine Hydrochloride, Bendeka (Bendamustine Hydrochloride), Besponsa (Inotuzumab Ozogamicin), Bevacizumab, Bexarotene, Bicalutamide, BiCNU (Carmustine), Binimetinib, Bleomycin Sulfate, Blinatumomab, Blincyto (Blinatumomab), Bortezomib, Bosulif (Bosutinib), Bosutinib, Braftovi (Encorafenib), Brentuximab Vedotin, Brigatinib, BuMel, Busulfan, Busulfex (Busulfan), Cabazitaxel, Cablivi (Caplacizumab-yhdp), Cabometyx (Cabozantinib-S-Malate), Cabozantinib-S-Malate, Calaspargase Pegol-mknl, Calquence (Acalabrutinib), Campath (Alemtuzumab), Camptosar (Irinotecan Hydrochloride), Capecitabine, Caplacizumab-yhdp, Carac (Fluorouracil—Topical), Carboplatin, Carfilzomib, Carmustine, Carmustine Implant, Casodex (Bicalutamide), Cemiplimab-rwlc, Ceritinib, Cerubidine (Daunorubicin Hydrochloride), Cervarix (Recombinant HPV Bivalent Vaccine), Cetuximab, Chlorambucil, Cisplatin, Cladribine, Clofarabine, Clolar (Clofarabine), Cobimetinib, Cometriq (Cabozantinib-S-Malate), Copanlisib Hydrochloride, Copiktra (Duvelisib), Cosmegen (Dactinomycin), Cotellic (Cobimetinib), Crizotinib, Cyclophosphamide, Cyramza (Ramucirumab), Cytarabine, Cytarabine Liposome, Dabrafenib Mesylate, Dacarbazine, Dacogen (Decitabine), Dacomitinib, Dactinomycin, Daratumumab, Darbepoetin Alfa, Darzalex (Daratumumab), Dasatinib, Daunorubicin Hydrochloride, Daunorubicin Hydrochloride and Cytarabine Liposome, Daurismo (Glasdegib Maleate), Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Durvalumab, Duvelisib, Efudex (Fluorouracil—Topical), Eligard (Leuprolide Acetate), Elitek (Rasburicase), Ellence (Epirubicin Hydrochloride), Elotuzumab, Eloxatin (Oxaliplatin), Eltrombopag Olamine, Elzonris (Tagraxofusp-erzs), Emapalumab-lzsg, Emend (Aprepitant), Empliciti (Elotuzumab), Enasidenib Mesylate, Encorafenib, Enzalutamide, Epirubicin Hydrochloride, Epoetin Alfa, Epogen (Epoetin Alfa), Erbitux (Cetuximab), Erdafitinib, Eribulin Mesylate, Erivedge (Vismodegib), Erleada (Apalutamide), Erlotinib Hydrochloride, Erwinaze (Asparaginase *Erwinia chrysanthemi*), Ethyol (Amifostine) Etopophos (Etoposide Phosphate), Etoposide, Etoposide Phosphate, Everolimus Evista (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), Femara (Letrozole), Filgrastim, Firmagon (Degarelix), Fludarabine Phosphate, Fluoroplex (Fluorouracil—Topical), Fluorouracil Injection, Fluorouracil-Topical, Flutamide, Folotyn (Pralatrexate), Fostamatinib Disodium, Fulvestrant, Fusilev (Leucovorin Calcium), Gamifant (Emapalumab-lzsg), Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, Gemtuzumab Ozogamicin, Gemzar (Gemcitabine Hydrochloride), Gilotrif (Afatinib Dimaleate), Gilteritinib Fumarate, Glasdegib Maleate, Gleevec (Imatinib Mesylate), Gliadel Wafer (Carmustine Implant), Glucarpidase, Goserelin Acetate, Granisetron, Granisetron Hydrochloride, Granix (Filgrastim), Halaven (Eribulin Mesylate), Hemangeol (Propranolol Hydrochloride), Herceptin Hylecta (Trastuzumab and Hyaluronidase-oysk), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Ibrance (Palbociclib), Ibritumomab Tiuxetan, Ibrutinib, Iclusig (Ponatinib Hydrochloride), Idamycin PFS (Idarubicin Hydrochloride), Idarubicin Hydrochloride, Idelalisib, Idhifa (Enasidenib Mesylate), Ifex (Ifosfamide), Ifosfamide, IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iobenguane I 131, Ipilimumab, Iressa (Gefitinib), Irinotecan Hydrochloride, Irinotecan Hydrochloride Liposome, Istodax (Romidepsin), Ivosidenib, Ixabepilone, Ixazomib Citrate, Ixempra (Ixabepilone), Jakafi (Ruxolitinib Phosphate), Jevtana (Cabazitaxel), Kadcyla (Ado-Trastuzumab Emtansine), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Larotrectinib Sulfate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Levulan Kerastik (Aminolevulinic Acid Hydrochloride), Libtayo (Cemiplimab-rwlc), Lomustine, Lonsurf (Trifluridine and Tipiracil Hydrochloride), Lorbrena (Lorlatinib), Lorlatinib, Lumoxiti (Moxetumomab Pasudotox-tdfk), Lupron (Leuprolide Acetate), Lupron Depot (Leuprolide Acetate), Lutathera (Lutetium Lu 177-Dotatate), Lutetium (Lu 177-Dotatate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Mektovi (Binimetinib), Melphalan, Melphalan Hydrochloride, Mercaptopurine, Mesna, Mesnex (Mesna), Methotrexate, Methylnaltrexone Bromide, Midostaurin, Mitomycin C, Mitoxantrone Hydrochloride, Mogamulizumab-kpkc, Moxetumomab Pasudotox-tdfk, Mozobil (Plerixafor), Mustargen (Mechlorethamine Hydrochloride), Mvasi (Bevacizumab), Myleran (Busulfan), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nplate (Romiplostim), Obinutuzumab, Odomzo (Sonidegib), Ofatumumab, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), Osimertinib Mesylate, Oxaliplatin, Paclitaxel, Paclitaxel Albumin-stabilized Nanoparticle Formulation Palbociclib, Palifermin, Palonosetron Hydrochloride, Palonosetron Hydrochloride and Netupitant, Pamidronate Disodium, Panitumumab, Panobinostat, Pazopanib Hydrochloride, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Piqray (Alpelisib), Plerixafor, Polatuzumab Vedotin-piiq, Polivy (Polatuzumab Vedotin-piiq), Pomalidomide, Pomalyst (Pomalidomide), Ponatinib Hydrochloride, Portrazza (Necitumumab), Poteligeo (Mogamulizumab-kpkc), Pralatrexate, Prednisone, Procarbazine Hydrochloride, Procrit (Epoetin Alfa), Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, Ravulizumab-cwvz, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), Retacrit (Epoetin Alfa), Revlimid (Lenalidomide), Rheumatrex (Methotrexate), Ribociclib, Rituxan (Rituximab), Rituxan Hycela (Rituximab and Hyaluronidase Human), Rituximab, Rituximab and Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sancuso (Granisetron), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), Sterile Talc Powder (Talc), Steritalc (Talc), Stivarga (Regorafenib), Sunitinib Malate, Sustol (Granisetron), Sutent (Sunitinib Malate), Sylatron (Peginterferon Alfa-2b), Sylvant (Siltuximab), Synribo (Omacetaxine Mepesuccinate), Tabloid (Thioguanine), Tafinlar (Dabrafenib Mesylate), Tagraxofusp-erzs, Tagrisso (Osimertinib Mesylate), Talazoparib Tosylate, Talc, Talimogene Laherparepvec, Talzenna (Talazoparib Tosylate), Tamoxifen Citrate, Tarceva (Erlotinib Hydrochloride), Targretin (Bexarotene), Tasigna (Nilotinib), Tavalisse (Fostamatinib Disodium), Taxol (Paclitaxel), Taxotere (Docetaxel), Tecentriq (Atezolizumab), Temodar (Temozolomide), Temozolomide, Temsirolimus, Thalidomide, Thalomid (Thalidomide), Thioguanine, Thiotepa, Tibsovo (Ivosidenib), Tisagenlecleucel, Tocilizumab, Tolak (Fluorouracil—Topical), Topotecan Hydrochloride, Toremifene, Torisel (Temsirolimus), Totect (Dexrazoxane Hydrochloride), Trabectedin, Trametinib, Trastuzumab, Trastuzumab and Hyaluronidase-oysk, Treanda (Bendamustine Hydrochloride), Trexall (Methotrexate), Trifluridine and Tipiracil Hydrochloride, Trisenox (Arsenic Trioxide), Tykerb (Lapatinib Ditosylate), Ultomiris (Ravulizumab-cwvz), Unituxin (Dinutuximab), Uridine Triacetate, Valrubicin, Valstar (Valrubicin), Vandetanib, Varubi (Rolapitant Hydrochloride), Vectibix (Panitumumab), VeIP, Velcade (Bortezomib), Vemurafenib, Venclexta (Venetoclax), Venetoclax, Verzenio (Abemaciclib), Vidaza (Azacitidine), Vinblastine Sulfate, Vincristine Sulfate, Vincristine Sulfate Liposome, Vinorelbine Tartrate, Vismodegib, Vistogard (Uridine Triacetate), Vitrakvi (Larotrectinib Sulfate), Vizimpro (Dacomitinib), Voraxaze (Glucarpidase), Vorinostat, Votrient (Pazopanib Hydrochloride), Vyxeos (Daunorubicin Hydrochloride and Cytarabine Liposome), Xalkori (Crizotinib), Xeloda (Capecitabine), Xgeva (Denosumab), Xofigo (Radium 223 Dichloride), Xospata (Gilteritinib Fumarate), Xtandi (Enzalutamide), Yervoy (Ipilimumab), Yescarta (Axicabtagene Ciloleucel), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), Zytiga (Abiraterone Acetate), and derivatives thereof.

Pharmaceutical Compositions

Methods for treatment of cancer and hyperproliferative diseases described herein include administering a therapeutically effective amount of a compound described herein. A compound described herein can be formulated in pharmaceutical compositions. Additionally, in certain embodiments, the subject is administered one or more additional pharmaceutical compositions comprising one or more additional anti-cancer agents. These compositions can comprise, in addition to a compound described herein and/or anti-cancer agent, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g., oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives can be included, as required.

The pharmaceutically useful compound according to the present invention that is to be given to an individual, administration is preferably in a "therapeutically effective amount" or "prophylactically effective amount" (as the case can be, although prophylaxis can be considered therapy), this being sufficient to show benefit to the individual. The actual amount administered, and rate and time-course of administration, will depend on the nature and severity of protein aggregation disease being treated. Prescription of treatment, e.g. decisions on dosage etc., is within the responsibility of general practitioners and other medical doctors, and typically takes account of the disorder to be treated, the condition of the individual subject, the site of delivery, the method of administration and other factors known to practitioners. Examples of the techniques and protocols mentioned above can be found in Remington's Pharmaceutical Sciences, 16th edition, Osol, A. (ed), 1980.

EXAMPLES

Below are examples of specific embodiments for carrying out the methods described in this disclosure. The examples are offered for illustrative purposes only and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B(1992).

Figure 12:
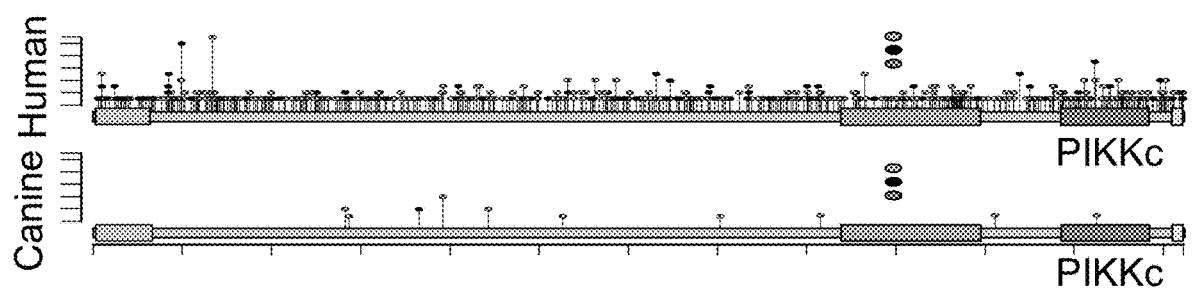
FIG. 12: is an illustration showing the analysis of ATM mutations in The Cancer Genome Atlas (TCGA), Pan Cancer Atlas. TOP: Information available through cBioPortal for Cancer Genomics (https://www.cbioportal.org/) was used to examine the spectrum of ATM mutations in human cancer. Mutations appear across the coding sequence with few hotspots. Of 10967 tumor samples from 32 histologies, 554 (5.1%) harbored mutations in ATM. BOTTOM: Pattern of mutation observed in canine cancer in the dataset. Mutations appear across histologies and like the human gene, interspersed along the coding sequence. Mutation was observed in 7.65% of tumors. The Ala989Val mutation occurs in Labrador Retrievers and Labrador mixed breed dogs and may therefore be an unconfirmed SNP of unknown functional significance. TAN: Tell/ATM N-Terminal motif, FAT: FRAP-ATM-TRRAP interaction domain, PIKKc: PI3K-related serine/threonine protein kinase domain.

Example 1: Treatment of Cancers Harboring Sporadic Mutations in the ATM Serine/Threonine Kinase Methods Both DNA-based and RNA-based molecular profiling was performed. For the DNA analysis, the prevalence of ATM mutations in a canine, pan-cancer dataset using next generation sequencing methods was analyzed. DNA was isolated for all samples from tissue collected through veterinarians enrolling a patient for genomic and/or transcriptomic analysis. The methodology was left to veterinarian discretion, as most soft tissue biopsies are suitable for analysis. However, all samples in this study were paraffin-embedded tissues submitted as one hematoxylin & eosin stained slide, plus 15-20 unstained sections. Tissue processing and pathology consultation were carried out prior to DNA isolation directly from DNA from paraffin-embedded tissues. Treatment data regarding ATM mutation and subject response to HDAC inhibition is monitored Results Sporadic occurrence of ATM mutation in multiple cancers (7/70 cases, 10%) was found Tables 1 and 2 and FIG. 12. ATM mutation was observed in both lymphoid/hematopoietic and solid malignancies. ATM mutations observed included missense, splice site and frameshift variants.

Conclusions

The prevalence and varied histology of the cancers in which we found ATM mutation mimics findings in human cancer. This is an important observation as ATM defects can be exploited to enhance anticancer therapy. For example, ATM mutant cells, with defective induction of DNA-repair, can be particularly susceptible to DNA damage induced cell death. Some histone deacetylase complex (HDAC) inhibitors potently induce reactive oxygen species and DNA damage. Combining a standard DNA damaging chemotherapeutic with an HDAC inhibitor can provide particularly potent treatment options for ATM mutant tumors.

Example 2: Treatment of Canine Cancers with Rapamycin

Canine subjects with cancer were treated with Rapamycin alone or in combination with other anti-cancer agents (Tables 3 and 12-26). The subjects were administered Rapamycin orally with a starting dose of 0.1 mg/kg/day and were monitored for disease progression compared to historical controls. There is a significant improvement in overall survival in subjects treated with Rapamycin compared to control subjects.

Example 3: Number and Type of Adverse Effects Reported in Canines Treated with Rapamycin Canine subjects with cancer were treated with pharmaceutical compositions comprising Rapamycin and were monitored for adverse effects including: diarrhea, vomiting inappetence, lethargy, skin lesions, progressive liver enzyme evaluations, increased cardiac toxicity and hemorrhagic gastroenteritis. Out of 192 canine subjects, 21% of the subjects with clinically reported outcomes experienced adverse effects (Tables 26 and 27).

Example 4: Treatment of Canine Cancers with Dasatinib

Canine subjects with cancer were treated with Dasatinib alone or in combination with other anti-cancer agents (Tables 4 and 12-26). The subjects were administered Dasatinib orally with a starting dose of 0.5-0.7 mg/kg/day and were monitored for disease progression compared to historical controls. There is a significant improvement in overall survival in subjects treated with Dasatinib compared to control subjects.

Example 5: Number and Type of Adverse Effects Reported in Canines Treated with Dasatinib Canine subjects with cancer were treated with pharmaceutical compositions comprising Dasatinib and were monitored for adverse effects including: diarrhea, vomiting inappetence, lethargy, skin lesions, progressive liver enzyme evaluations, increased cardiac toxicity and hemorrhagic gastroenteritis. Out of 94 canine subjects, 31% of the subjects with clinically reported outcomes experienced adverse effects (Tables 26 and 27).

Example 6: Treatment of Canine Cancers with Lapatinib

Canine subjects with cancer were treated with Lapatinib alone or in combination with other anti-cancer agents (Tables 5 and 12-26). The subjects were administered Lapatinib orally with a starting dose of 5-10 mg/kg/day and were monitored for disease progression compared to historical controls. There is a significant improvement in overall survival in subjects treated with Lapatinib compared to control subjects.

Example 7: Number and Type of Adverse Effects Reported in Canines Treated with Lapatinib Canine subjects with cancer were treated with pharmaceutical compositions comprising Lapatinib and were monitored for adverse effects including: diarrhea, vomiting inappetence, lethargy, skin lesions, progressive liver enzyme evaluations, increased cardiac toxicity and hemorrhagic gastroenteritis. Out of 162 canine subjects, 22% of the subjects with clinically reported outcomes experienced adverse effects (Tables 26 and 27).

Example 8: Treatment of Canine Cancers with Trametinib

Canine subjects with cancer were treated with Trametinib alone or in combination with other anti-cancer agents (Tables 6 and 12-26). The subjects were administered Trametinib orally with a starting dose of 0.02 mg/kg/day and were monitored for disease progression compared to historical controls. There is a significant improvement in overall survival in subjects treated with Trametinib compared to control subjects.

Example 9: Number and Type of Adverse Effects Reported in Canines Treated with Trametinib Canine subjects with cancer were treated with pharmaceutical compositions comprising Trametinib and were monitored for adverse effects including: diarrhea, vomiting inappetence, lethargy, skin lesions, progressive liver enzyme evaluations, increased cardiac toxicity and hemorrhagic gastroenteritis. Out of 275 canine subjects, 24% of the subjects with clinically reported outcomes experienced adverse effects (Tables 26 and 27).

Example 10: Treatment of Canine Cancers with Vorinostat

Canine subjects with cancer were treated with Vorinostat alone or in combination with other anti-cancer agents (Tables 7 and 12-26). The subjects were administered Vorinostat orally with a starting dose of 30-60 mg/kg/every other day and were monitored for disease progression compared to historical controls. There is a significant improvement in overall survival in subjects treated with Vorinostat compared to control subjects.

Example 11: Number and Type of Adverse Effects Reported in Canines Treated with Vorinostat Canine subjects with cancer were treated with pharmaceutical compositions comprising Vorinostat and were monitored for adverse effects including: diarrhea, vomiting inappetence, lethargy, skin lesions, progressive liver enzyme evaluations, increased cardiac toxicity and hemorrhagic gastroenteritis. Out of 89 canine subjects, 34% of the subjects with clinically reported outcomes experienced adverse effects (Tables 27 and 28).

Example 12: Treatment of Canine Cancers with Imatinib

Canine subjects with cancer were treated with Imatinib alone or in combination with other anti-cancer agents (Table 8). The subjects were administered Imatinib orally with a starting dose of 10 mg/kg/day and were monitored for disease progression compared to historical controls. There is a significant improvement in overall survival in subjects treated with Imatinib compared to control subjects.

Example 13: Number and Type of Adverse Effects Reported in Canines Treated with Imatinib Canine subjects with cancer were treated with pharmaceutical compositions comprising Imatinib and were monitored for adverse effects including: diarrhea, vomiting inappetence, lethargy, skin lesions, progressive liver enzyme evaluations, increased cardiac toxicity and hemorrhagic gastroenteritis. Out of 83 canine subjects, 24% of the subjects with clinically reported outcomes experienced adverse effects (Tables 27 and 28).

Example 14: Treatment of Canine Cancers with Crizotinib

Canine subjects with cancer were treated with Crizotinib alone or in combination with other anti-cancer agents (Table 9 and 12-26). The subjects were administered Crizotinib orally with a starting dose of 1 mg/kg/day-2 mg/kg/day and were monitored for disease progression compared to historical controls. There is a significant improvement in overall survival in subjects treated with Crizotinib compared to control subjects.

Example 15: Number and Type of Adverse Effects Reported in Canines Treated with Crizotinib Canine subjects with cancer were treated with pharmaceutical compositions comprising Crizotinib and were monitored for adverse effects including: diarrhea, vomiting inappetence, lethargy, skin lesions, progressive liver enzyme evaluations, increased cardiac toxicity and hemorrhagic gastroenteritis. Out of 9 canine subjects, 43% of the subjects with clinically reported outcomes experienced adverse effects (Tables 27 and 28).

Example 16: Treatment of canine cancers with Sorafenib

Canine subjects with cancer were treated with Sorafenib alone or in combination with other anti-cancer agents (Tables 10 and 12-26). The subjects were administered Sorafenib orally with a starting dose of 1 mg/kg/day-3 mg/kg/day or 1 mg/kg/day-3 mg/kg/week and were monitored for disease progression compared to historical controls. There is a significant improvement in overall survival in subjects treated with Sorafenib compared to control subjects.

Example 17: Number and Type of Adverse Effects Reported in Canines Treated with Sorafenib Canine subjects with cancer were treated with pharmaceutical compositions comprising Sorafenib and were monitored for adverse effects including: diarrhea, vomiting inappetence, lethargy, skin lesions, progressive liver enzyme evaluations, increased cardiac toxicity and hemorrhagic gastroenteritis. A minority of subjects with clinically reported outcomes experience adverse effects.

Example 18: Increased Median Survival of Canine Subjects with Cancers after Treatment with Targeted Therapies The median survival of subjects treated with targeted therapies comprising, HDAC inhibitors, Rapamycin, Dasatinib, Lapatinib, Trametinib, Vorinostat, Imatinib, Crizotinib, Sorafenib, and combinations thereof versus subjects treated with traditional non-targeted therapies was determined (FIG. 1). There was an increase in median survival in subjects with transitional cell carcinoma, thyroid cancer, squamous cell carcinoma, soft tissue sarcoma, pulmonary adenocarcinoma, osteosarcoma, melanoma, mast cell tumor, histiocytic sarcoma, hepatocellular carcinoma and AGASACA.

Example 19: Increased Survival of Canine Subjects with Splenic Hemangiosarcoma Treated with Targeted Therapies Survival of subjects with splenic hemangiosarcoma that have been either treated with chemotherapy and splenectomy alone ("control") or treated with targeted therapy and chemotherapy and splenectomy ("treated") was determined (FIG. 2). There was a significant increase in the probability of survival in subjects treated with targeted therapies versus patients with splenectomy and traditional chemotherapy alone.

Example 20: Increased Survival of Canine Subjects with Transitional Cell Carcinoma and/or Urinary Cancer Harboring BRAF Mutations Canine subjects with Transitional Cell Carcinoma (TCC) and/or Urinary Cancer (UC) harboring a BRAF mutation were treated with targeted drugs (Trametinib, Lapatinib or Lapatinib and Trametinib) with or without standard chemotherapy and a COX2 inhibitor (FIG. 3). Trametinib was administered at a dose of 0.02-0.03 mg/kg orally, daily. Lapatinib was administered at a dose of 5-10 mg/kg orally once daily. Subjects treated with the targeted drugs exceeded published median survival times (MST) for either Cox inhibitor treatment alone (195 days) or chemotherapy and Cox2 inhibitor treatment (291 days).

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

Tables

Lengthy table referenced here

US12186393-20250107-T00001

Please refer to the end of the specification for access instructions.

Lengthy table referenced here

US12186393-20250107-T00002

Please refer to the end of the specification for access instructions.

Lengthy table referenced here

US12186393-20250107-T00003

Please refer to the end of the specification for access instructions.

Lengthy table referenced here

US12186393-20250107-T00004

Please refer to the end of the specification for access instructions.

Lengthy table referenced here

US12186393-20250107-T00005

Please refer to the end of the specification for access instructions.

Lengthy table referenced here

US12186393-20250107-T00006

Please refer to the end of the specification for access instructions.

Lengthy table referenced here

US12186393-20250107-T00007

Please refer to the end of the specification for access instructions.

Lengthy table referenced here

US12186393-20250107-T00008

Please refer to the end of the specification for access instructions.

Lengthy table referenced here

US12186393-20250107-T00009

Please refer to the end of the specification for access instructions.

Lengthy table referenced here

US12186393-20250107-T00010

Please refer to the end of the specification for access instructions.

Lengthy table referenced here

US12186393-20250107-T00011

Please refer to the end of the specification for access instructions.

Lengthy table referenced here

US12186393-20250107-T00012

Please refer to the end of the specification for access instructions.

Lengthy table referenced here

US12186393-20250107-T00013

Please refer to the end of the specification for access instructions.

Lengthy table referenced here

US12186393-20250107-T00014

Please refer to the end of the specification for access instructions.

Lengthy table referenced here

US12186393-20250107-T00015

Please refer to the end of the specification for access instructions.

Lengthy table referenced here

US12186393-20250107-T00016

Please refer to the end of the specification for access instructions.

Lengthy table referenced here

US12186393-20250107-T00017

Please refer to the end of the specification for access instructions.

Lengthy table referenced here

US12186393-20250107-T00018

Please refer to the end of the specification for access instructions.

Lengthy table referenced here

US12186393-20250107-T00019

Please refer to the end of the specification for access instructions.

Lengthy table referenced here

US12186393-20250107-T00020

Please refer to the end of the specification for access instructions.

Lengthy table referenced here

US12186393-20250107-T00021

Please refer to the end of the specification for access instructions.

Lengthy table referenced here

US12186393-20250107-T00022

Please refer to the end of the specification for access instructions.

Lengthy table referenced here

US12186393-20250107-T00023

Please refer to the end of the specification for access instructions.

Lengthy table referenced here

US12186393-20250107-T00024

Please refer to the end of the specification for access instructions.

Lengthy table referenced here

US12186393-20250107-T00025

Please refer to the end of the specification for access instructions.

Lengthy table referenced here

US12186393-20250107-T00026

Please refer to the end of the specification for access instructions.

Lengthy table referenced here

US12186393-20250107-T00027

Please refer to the end of the specification for access instructions.

Lengthy table referenced here

US12186393-20250107-T00028

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US12186393B2). An electronic copy of the table will also be available from the USPTO upon request and payment of the fee set forth in 37 CFR 1.19(b)(3).

The invention claimed is:

1. A method of treating transitional cell carcinoma in a canine subject, comprising: administering to the canine subject in need thereof a therapeutically effective amount of a pharmaceutical composition comprising Lapatinib, wherein the transitional cell carcinoma harbors at least one mutation in BRAF.

2. The method of claim 1, wherein the Lapatinib is administered at a dose equal to or less than 50 mg/kg.

3. The method of claim 1, wherein the Lapatinib is administered at a frequency selected from the group consisting of, twice daily, once daily, once every other day, once every third day, once every fourth day, once every $5^{th}$ day, or weekly.

4. The method of claim 1, wherein the Lapatinib is administered orally.

5. The method of claim 1, further comprising administering a therapeutically effective amount of at least one additional anti-cancer agent.

6. The method of claim 5, wherein the at least one additional anti-cancer agent is a DNA-damaging chemotherapeutic agent.

7. The method of claim 6, wherein the DNA-damaging chemotherapeutic agent is selected from the group consisting of: a DNA-alkylating agent, a DNA-crosslinking agent, an antimetabolite, a topoisomerase inhibitor, and a DNA-intercalating agent.

8. The method of claim 5, wherein the at least one additional anti-cancer agent is a targeted anti-cancer agent.

9. The method of claim 8, wherein the targeted anti-cancer agent is selected from the group consisting of Crizotinib, Erlotinib, Gefinitib, Imatinib, Dasatinib, Rapamycin, Sorafenib, Trametinib, and Vorinostat.

10. The method of claim 9, wherein the targeted anti-cancer agent is Trametinib.

11. The method of claim 1, further comprising performing surgery on the subject.

12. The method of claim 1, further comprising administering to the subject ionizing radiation.

13. The method of claim 1, further comprising having determined from a biological sample derived from the cancer, that the cancer harbors a mutation in at least BRAF.

14. The method of claim 13, wherein the biological sample is a nucleic acid sample.

15. The method of claim 14, wherein the biological sample is a purified nucleic acid sample.

16. The method of claim 15, wherein the sample is DNA.

17. The method of claim 15, wherein the sample is RNA.

18. The method of claim 13, wherein the determining of the mutation in the at least one gene is performed by sequencing the nucleic acid sample.

19. The method of claim 1, wherein the cancer harbors at least one additional mutation in at least one gene shown in Tables 1, 2 and 12-26.

20. The method of claim 13, further comprising determining or having determined from a biological sample derived from the cancer, at least one additional mutation in at least one gene shown in Tables 1, 2, and 12-26.

* * * * *